US006638502B1

(12) United States Patent
Li et al.

(10) Patent No.: US 6,638,502 B1
(45) Date of Patent: Oct. 28, 2003

(54) ADENOVIRUS-MEDIATED INTRATUMORAL DELIVERY OF AN ANGIOGENESIS ANTAGONIST FOR THE TREATMENT OF TUMORS

(75) Inventors: Hong Li, Epinay sur Seine (FR); He Lu, Epinay sur Seine (FR); Frank Griscelli, Paris (FR); Paule Opolon, Paris (FR); Claudine Soria, Taverny (FR); Thierry Ragot, Meudon (FR); Yves Legrand, Paris (FR); Jeannette Soria, Taverny (FR); Christelle Mabilat, Corbeil Essonnes (FR); Michel Perricaudet, Ecrosnes (FR); Patrice Yeh, Gif sur Yvette (FR)

(73) Assignee: Gencell SAS, Vitry sur Seine (FR)

(*) Notice: Subject to any disclaimer, the term of this patent is extended or adjusted under 35 U.S.C. 154(b) by 0 days.

(21) Appl. No.: 09/403,736

(22) PCT Filed: Apr. 27, 1998

(86) PCT No.: PCT/EP98/02491

§ 371 (c)(1),
(2), (4) Date: Jun. 29, 2000

(87) PCT Pub. No.: WO98/49321

PCT Pub. Date: Nov. 5, 1998

Related U.S. Application Data
(60) Provisional application No. 60/044,980, filed on Apr. 28, 1997.

(51) Int. Cl.[7] ........................ A61K 48/00; C12N 15/86; C12N 15/861
(52) U.S. Cl. ........................ 424/93.2; 514/44; 435/455; 435/456; 435/320.1
(58) Field of Search .................. 514/44; 536/23.5; 435/235.1, 456, 320.1, 455; 424/93.2

(56) References Cited

U.S. PATENT DOCUMENTS

| | | | |
|---|---|---|---|
| 4,650,764 A | 3/1987 | Temin et al. | 435/350 |
| 4,797,368 A | 1/1989 | Carter et al. | 435/320.1 |
| 4,814,470 A | 3/1989 | Colin et al. | 514/449 |
| 4,857,653 A | 8/1989 | Colin et al. | 549/511 |
| 4,861,719 A | 8/1989 | Miller | 435/236 |
| 4,924,011 A | 5/1990 | Denis et al. | 549/510 |
| 4,980,289 A | 12/1990 | Temin et al. | 435/235.1 |
| 5,124,263 A | 6/1992 | Temin et al. | 435/349 |
| 5,139,941 A | 8/1992 | Muzyczka et al. | 435/456 |
| 5,168,062 A | 12/1992 | Stinski | 435/366 |
| 5,290,957 A | 3/1994 | Correa et al. | 549/510 |
| 5,292,921 A | 3/1994 | Correa et al. | 560/29 |
| 5,385,839 A | 1/1995 | Stinski | 435/366 |
| 5,399,346 A | 3/1995 | Anderson et al. | 424/93.21 |
| 5,438,072 A | 8/1995 | Bobee et al. | 514/449 |
| 5,459,127 A | 10/1995 | Felgner et al. | 514/7 |
| 5,580,859 A | 12/1996 | Felgner et al. | 514/44 |
| 5,587,493 A | 12/1996 | Bouchard et al. | 549/510 |
| 5,589,466 A | 12/1996 | Felgner et al. | 514/44 |
| 5,639,725 A | 6/1997 | O'Reilly et al. | 514/12 |
| 5,652,095 A * | 7/1997 | Taniguchi et al. | 435/6 |
| 5,885,795 A * | 3/1999 | O'Reilly et al. | 435/69.1 |
| 6,080,728 A * | 6/2000 | Mixson | 514/44 |
| 6,143,290 A * | 11/2000 | Zhang et al. | 424/93.2 |
| 6,251,433 B1 * | 6/2001 | Zuckermann et al. | 424/486 |

FOREIGN PATENT DOCUMENTS

| | | |
|---|---|---|
| CA | 2012311 | 3/1990 |
| EP | 185 573 | 6/1986 |
| EP | 253 738 | 7/1987 |
| EP | 453 242 | 4/1990 |
| EP | 178 220 | 2/1992 |
| EP | 488 528 | 11/1995 |
| FR | 2726285 | 5/1996 |
| WO | WO 89/07150 | 8/1989 |
| WO | WO 90/02806 | 3/1990 |
| WO | WO 91/17976 | 11/1991 |
| WO | WO 91/18088 | 11/1991 |
| WO | WO 92/05263 | 4/1992 |
| WO | WO 93/00928 | 1/1993 |
| WO | WO 93/00929 | 1/1993 |
| WO | WO 93/09239 | 5/1993 |
| WO | WO 93/15199 | 8/1993 |
| WO | WO 94/12649 | 6/1994 |
| WO | WO 95/18863 | 7/1994 |
| WO | WO 94/21807 | 9/1994 |
| WO | WO 94/26914 | 11/1994 |
| WO | WO 94/28152 | 12/1994 |
| WO | WO 94/28938 | 12/1994 |
| WO | WO 95/02697 | 1/1995 |
| WO | WO 95/07358 | 3/1995 |
| WO | WO 95/21931 | 8/1995 |
| WO | WO 95/28494 | 10/1995 |
| WO | WO 95/29242 | 11/1995 |
| WO | WO 96/01313 | 1/1996 |
| WO | WO 96/01815 | 1/1996 |
| WO | WO 96/17823 | 6/1996 |
| WO | WO 96/22378 | 7/1996 |
| WO | WO 96/25508 | 8/1996 |
| WO | WO 97/04092 | 2/1997 |
| WO | WO 97/15666 | 5/1997 |

OTHER PUBLICATIONS

Wilson, Vehicles for gene therapy, 1993, NAUTRE, vol. 365, pp. 691–692.*
Tanaka et al., "Viral vector–mediated transduction of modified platelet factor 4 cDNA inhibits angiogenesis and tumor growth," Nature Med. 3 (4): 437–442, Apr. 5, 1997.*

(List continued on next page.)

Primary Examiner—Scott D. Priebe
(74) Attorney, Agent, or Firm—Wiley Rein & Fielding LLP

(57) ABSTRACT

The present invention relates to gene therapy for the treatment of tumors. The invention more particularly relates to introduction of a gene encoding an anti-angiogenic factor into cells of a tumor, for example with a defective adenovirus vector, to inhibit growth or metastasis, or both, of the tumor. In a specific embodiment, delivery of a defective adenovirus that expresses the amino terminal fragment of urokinase (ATF) inhibited growth and metastasis of tumors. These effects were correlated with a remarkable inhibition of neovascularization within, and at the immediate vicinity of, the injection site. Delivery of a defective adenovirus vector that expresses kringles 1 to 3 of angiostatin inhibited tumor growth and tumorigenicity, and induced apoptosis of tumor cells. The invention further provides viral vectors for use in the methods of the invention.

14 Claims, 11 Drawing Sheets

OTHER PUBLICATIONS

Tanaka et al., "Retrovral and adenoviral mediated transduction fo angiostatin cDNA inhibits angiogenesis and tumor growth," Proc. Amer. Assoc. Cancer Res. 38: 264, Mar. 1997.*

Dang et al.Gene Therapy and Translational Cancer Therapy, Clinical Cancer Research, vol. 5, 471–474, Feb. 1999.*

Eck, S.L. et al., 1996, Ch. 5. Gene Based Therapy,Goodman & Gillman's The Pharmacological basis of Therapeutics. p. 77–101ck, et al.*

Robbins, Review: Viral Vectors for gene therapy, Trends in Biotechnology, vol. 16, pp. 35–40.*

Estreicher et al., The Receptor for Urokinase Type Plasminogen Activator Polarizes Expression of the Protease to the Leading Edge of Migrating Monocytes and Promotes Degradation of Enzyme Inhibitor Complexes, Journal of Cell Biology 111, 783–792 (1990).

Pepper et al., Chondrocytes Inhibit Endothelial Sprout Formation In Vitro: Evidence for Involvement of a Transforming Growth Factor–Beta, Journal of Cellular Physiology 146, 170–179 (1991).

Ploug et al., Cellular Receptor for Urokinase Plasminogen Activator, The Journal of Biological Chemistry 266(3), 1926–1933 (1991).

Ellis et al., Plasminogen Activation by Receptor–bound Urokinase, The Journal of Biological Chemistry 266(19), 12752–12758 (1991).

Wei et al., Identification of the Urokinase Receptor as an Adhesion Receptor for Vitronectin, The Journal of Biological Chemistry 269(51), 32380–32388 (1994).

Appella et al., The Receptor–binding Sequence of Urokinase: A Biological Function for the Growth–Factor Module of Proteases, The Journal of Biological Chemistry 262(10), 4437–4440 (1987).

Cao et al., Kringle Domains of Human Angiostatin, The Journal of Biological Chemistry 271(46), 29461–29467 (1996).

Imren et al., Overexpression of Tissue Inhibitor of Metalloproteinases–2 by Retroviral–mediated Gene Transfer in Vivo Inhibits Tumor Growth and Invasion, Cancer Research 56, 2891–2895 (1996).

Shapiro et al., Induction of Primary Cutaneous Melanocytic Neoplasms in Urokinase–Type Plasminogen Activator (uPA)–deficient and Wild–Type Mice: Cellular Blue Nevi Invade but Do Not Progress to Malignant Melanoma in uPA–deficient Animals, Cancer Research 56, 3597–3604 (1996).

Skladanowski et al., Expression of Wild–Type p53 Increases Etopside Cytotoxicity in M1 Myeloid Leukemia Cells by Facilitated G2 to M Transtition: Implication for Gene Therapy, Cancer Research 57, 818–823 (1997).

Sim et al., A Recombinant Human Angiostatin Protein Inhibits Experimental Primary and Metastatic Cancer, Cancer Research 57, 1329–1334 (1997).

Liotta et al., Quantitative Relationships of Intravascular Tumor Cells, Tumor Vessels, and Pulmonary Metastases folling Tumor Implantation, Cancer Research 34, 997–1004 (1974).

Hori et al., Suppression of Solid Tumor Growth by Immunoneutralizing Monoclonal Antibodies against Human Basic Fibroblast Growth Factor, Cancer Research 51, 6180–6184 (1991).

Min et al., Urokinase Receptor Antagonists Inhibit Angiogenesis and Primary Tumor in Syngeneic Mice, Cancer Research 56, 2428–2433 (1996).

Wei et al., Regulation of Integrin Function by the Urokinase Receptor, Science 273, 1551–1555 (1996).

Graeber et al., Hypoxia–mediated selection of cells with diminished apoptotic potential in solid tumours, Nature 379, 88–91 (1996).

Bacharach et al., In vivo patterns of expression of urokinase and its inhibitor PAI–1 suggest a concerted role in regulating physiological angiogenesis, Proc. Natl. Acad. Sci. USA 89: 10686–10690 (1989).

He et al., Tissue cooperation in a proteolytic cascade activating human interstitial collagenase, Proc. Natl. Acad. Sci. 86, 2632–2636 (1989).

Crowley et al., Prevention of metastasis by inhibition of the urokinase receptor, Proc. Natl. Acad. Sci. 90, 5021–5025 (1993).

Davis et al., Monoclonal antibodies to mitotic cells, Proc. Natl. Acad. Sci. 80, 2926–2930 (1983).

Gupta et al., A potent inhibitor of endothelial cell proliferation is generated by proteolytic cleavage of the chemokine platelet factor 4, Proc. Natl. Acad. Sci 92, 7799–7803 (1995).

Mignatti et al., Biology & Biochemistry of Proteinases in Tumor Invasion, Physiological Reviews 73(1), 161–195 (1993).

Pyke et al., Urokinase–type Plasminogen Activator is Expressed in Stromal Cells and Its Receptor in Cancer Cells and Its Receptor in Cancer Cells at Invasive Foci in Human Colon Adenocarcinomas, American Journal of Pathology 138(5), 1059–1067 (1991).

Magdolen et al., Systematic mutational analysis of the receptor–binding region of the human urokinase–type plasminogen activator, Eur J. Biochem 237, 743–751 (1996).

Schmitt et al., Tumor–associated Proteases, Fibrinolysis 6(Suppl. 1), 3–26 (1992).

Stratford–Perricaude et al., Widespread Long–term Gene Transfer to Mouse Skeletal Muscles and Heart, J. Clin. Invest. 90, 626–630 (1992).

Weidner et al., Tumor Angiogenesis and Metastasis–Correlation in Invasive Breast Carcinoma, The New England Journal of Medicine 324(1), 1–8 (1991).

Hanahan et al., Patterns and Emerging Mechanisms of the Angiogenic Switch during Tumorigenesis, Cell 86, 353–364 (1996).

Wickham et al., Integrins avB3 and avB5 Promote Adenovirus Internalization but Not Virus Attachment, Cell 73, 309–319 (1993).

Brooks et al., Integrin avB3 Antagonists Promote Tumor Regression by Inducing Apoptosis of Angiogenic Blood Vessels, Cell 79, 1157–1164 (1994).

O'Reilly et al., Endostatin: An Endogenous Inhibitor of Angiogenesis and Tumor Growth, Cell 88, 277–285 (1997).

Dong et al., Macrophage–Derived Metalloelastase Is Responsible for the Generation of Angiostatin in Lewis Lung Carcinoma, Cell 88, 801–810 (1997).

King et al., Mitosis in Transition, Cell 79, 563–571 (1994).

Yeh et al., Advances in adenoviral vectors: from genetic engineering to their biology, FASEB 11, 615–623 (1997).

Folkman, What Is the Evidence That Tumors are Angiogenesis Dependent?, Journal of the National Cancer Institute 82(1), 4–6 (1990).

Mirshahi et al., Evaluation of the Inhibition by Heparin and Hirudin of Coagulation Activation During r–tPA–Induced Thrombolysis, Blood, 74(3), 1025–1030 (1989).

Plate et al., Vascular endothelial growth factor is a potential tumour angiogenesis factor in human gliomas in vivo, Nature 359, 845–848 (1992).

Roth et al., Gene Therapy for Cancer: What Have We Done and Where Are We Going?, Journal of the National Cancer Institute 89(1), 21–39 (1997).

Clapp et al., The 16–Kilodalton N–Terminal Fragment of Human Prolactin Is a Potent Inhibitor of Angiogenesis, Endocrinology 133(3), 1292–1299 (1993).

Kim et al., Inhibition of vascular endothelial growth factor–induced angiogenesis suppresses tumour growth in vivo, Nature 362, 841–844 (1993).

Hamada et al., Separable groth and migration factors for large–cell lymphoma cells secreted by microvascular endothelial cells derived from target organs for metastasis, Br. J. Cancer 66, 349–354 (1992).

Trochon et al., Evidence of Involvement of CD44 In Endothelial Cell Proliferation, Migration and Angiogenesis In Vivo, Int. J. Cancer 66, 664–668 (1996).

Fan et al., Controlling the vasculature: angiogensis, anti–angiogenesis and vascular targeting of gene therapy, TiPS 16, 57–66 (1995).

Rifkin et al., Growth factor control of extracellular proteolysis, Cell Differentiation & Development 32, 313–318 (1990).

Lu et al., Blockage of urokinase receptor reduces in vitro the motility and the deformability of endothelial cells, FEBS Letters 380, 21–24 (1996).

Kobayashi et al., Inhibition of Metastasis of Lewis Lung Carcinoma by A Synthetic Peptide Within Grown Factor–Like Domain of Urokinase In The Experimental and Spontaneous Metastasis Model, Int. J. Cancer 57, 727–733 (1994).

Lu et al., Blockage of the urokinase receptor on the cell surface: construction and characterization of a hybrid protein consisting of the N–terminal fragment of human urokinase and human albumin, FEBS Letters 356, 56–59 (1994).

Holmegren et al., Dormancy of micrometastases: Balanced proliferation and apoptosis in the presence of angiogenesis suppression, Nature Medicine 1(2), 149–153 (1995).

Graham et al., Characteristics of a Human Cell Line Transformed by DNA from Human Adenovirus Type 5, J. Gen. Virol. 36, 59–72 (1977).

Hayes et al., Carbohydrate of the Human Plasminogen Variants, The Journal of Biological Chemistry 254(18), 8772–8776 (1979).

Roldan et al., Cloning and expression of the receptor for human urokinase plasminogen activator, a central molecule in cell surface, plasmin dependent proteolysis, The EMBO Journal 9(2), 467–474 (1990).

Hirt, Selective Extraction of Polyoma DNA from Infected Mouse Cell Cultures, J. Mol. Biol. 26, 365–369 (1967).

Folkman, Angiogenesis in cancer, vascular, rheumatoid and other disease, Nature Medicine 1(1), 27–31 (1995).

Belin et al., Cloning, nucleotide sequencing and expression of cDNAs encoding mouse urokinase–type plasminogen activator, Eur. J. Biochem 148, 225–232 (1985).

Naldini et al., Extracellular proteolytic cleavage by urolinase is required for activation of hepatocyte growth factor/scatter factor, The EMBO Journal 11(13), 4825–4833 (1992).

O'Reilly et al., Angiostatin induces and sustains dormancy of human primary tumors in mice, Nature Medicine 2(6), 689–692 (1996).

Markowitz et al., A Safe Packaging Line for Gene Transfer: Separating Viral Genes on Two Different Plasmids, Journal of Virology 62(4), 1120–1124 (1988).

Kuo et al., Efficient Gene Transfer Into Primary Murine Lymphocytes Obviating the Need for Drug Selection, Blood 82(3), 845–852 (1993).

Machy et al., Gene transfer from targeted liposomes to specific lymphoid cells by electroporation, Proc. Natl. Acad. Sci. 85, 8027–8031 (1988).

Felgner et al., Lipofection: A highly efficient, lipid–mediated DNA–transfection procedure, Proc. Natl. Acad. Sci. 84, 7413–7417 (1987).

Bender et al., Evidence that the Packaging Signal of Moloney Murine Leukemia Virus Extends into the gag Region Journal of Virology 1639–1646 (1987).

Ulmer et al., Heterologous Protection Against Influenza by Injection of DNA Encoding a Viral Protein, Science 259, 1745–1749 (1993).

Le Gal La Salle et al., An Adenovirus Vector for Gene Transfer into Neurons and Glia in the Brain, Science 259, 988–990 (1993).

Samulski et al., A Recombinant Plasmid from Which an Infectious Adeno–Associated Virus Genome can be Excised in Vitro and Its use To Study Viral Replication, Journal of Virology 61(10), 3096–3101 (1987).

Dvorak et al., Iidentification and Characterization of the Blood Vessels of Solid Tumors That Are Leaky to Circulating Macromolecules, American Journal of Pathology 133(1), 95–109 (1988).

Readhead et al., Expression of a Myelin Basic Protein Gene in Transgenic Shiverer Mice: Correction of the Dysmyelinating Phenotype, Cell, 48, 703–712 (1987).

Kollias et al., Regulated Expression of Human A Gamma, Beta, and Hybrid Gamma Beta–Globin Genes in Trasgenic Mice: Manipulation of the Developmental Expression Patterns, Cell 46, 89–94, (1986).

Leder et al., Consequences of Widespread Deregulation of the c–myc Gene in Transgenic Mice: Multiple Neoplasms and Normal Development, Cell 45, 485–495 (1986).

Yamamoto et al., Identification of a Functional Promoter in the Long Terminal Repeat of Rous Sarcoma Virus, Cell 22, 787–797 (1980).

Mann et al., Construction of a Retrovirus Packaging Mutant and Its use to Produce Helper–Free Defective Retrovirus, Cell 33, 153–159 (1983).

Swift et al., Tissue–Specific Expression of the Rat Pancreatic Elastase I Gene in Transgenic Mice. Cell 38, 639–646 (1984).

Grosschedl et al., Introduction of a Micro Immunoglobulin Gene into the Mouse Germ Line: Specific Expression in Lymphoid Cells and Synthesis of Functional Antibody, Cell 38, 647–658 (1984).

Lebkowski et al., Adeno–Associated Virus: a Vector system for Efficient Introduction and Integration of DNA into a Variety of Mammalian Cell Types, Molecular & Cellular Biology 8(10), 3988–3996 (1988).

Alexander et al., Expression of the c–myc Oncogene under Control of an Immunoglobulin Enhancer in Eu–myc Transgenic Mice, Molecular & Cellular Biology 7(4), 1436–1444 (1987).

Krumlauf et al., Developmental Regulation of alpha–Fetoprotein Genes in Transgenic Mice, Molecular & Cellular Biology 5(7), 1639–1648 (1985).

Hammer et al., Diversity of Alpha–Fetoprotein Gene Expression in Mice Is Generated by a Combination of Separate Enhancer Elements, Science 235, 53–58 (1987).

Mason et al., The Hypogonadal Mouse: Reproductive Functions Restored by Gene Therapy, Science 234, 1372–1378 (1986).

Williams et al., Introduction of foreign genes into tissues of living mice by DNA–coated microprojectiles, Pro. Natl. Acad. Sci. 88, 2726–2730 (1991).

DeBoer et al., The tac promoter: A functional hybrid derived from the trp and lac promoters, Proc. Natl. Acad. Sci. 80, 21–25 (1983).

Villa–Komaroff et al., A bacterial clone synthesizing proinsulin, Proc. Natl. Acad. Sci. 75(8), 3727–3731 (1978).

Wagner et al., Nucleotide sequence of the thymidine kinase gene or herpes simplex virus type 1, Proc. Natl. Acad. Sci. 78(3), 1441–1445 (1981).

Hutchison et al., A complete library of point substitution mutations in the glucocorticoid response element of mouse mammary tumor virus, Proc. Natl. Acad. Sci. 83, 710–714 (1986).

Wu et al., Receptor–mediated Gene Delivery and Expression in Vivo, Journal of Biological Chemistry 263(29), 14621–14624 (1988).

Wilson et al., Hepatocyte–directed Gene Transfer in Vivo Leads to Transient Improvement of Hypercholesterolemia in Low Density Lipoprotein Receptor–deficient Rabbits, Journal of Biological Chemistry 267(2), 963–967 (1992).

Wu et al., Receptor–mediated in Vitro Gene Transformation by a Soluble Carrier DNA System, Journal of Biological Chemistry 262(10), 4429–4432 (1987).

Benoist et al., In vivo sequence requirements of th SV40 early promoter region, Nature 290, 304–310 (1981).

Brinster et al., Regulation of metallothinonein–thymidine kinase fusion plasmids injected into mouse eggs, Nature 296, 39–42 (1982).

Shani, Tissue–specific expression of rat myosin light–chain 2 gene in transgenic mice, Nature 314, 283–286 (1985).

Hanahan, Heritable formation of pancreatice Beta–cell tumours in transgenic mice expressing recombinant insulin/simian virus 40 oncogenes, Nature 315, 115–122 (1985).

Magram et al., Developmental regulation of a cloned adult Beta–globin gene in transgenic mice, Nature 315, 338–340 (1985).

Gilbert et al., Useful Proteins from Recombinant Bacteria, Scientific American 242(4), 74–94 (1980).

Kaplitt et al., Expression of a Functional Foreign Gene in Adult Mammalian Brain following in Vivo Transfer via a Herpes Simplex Virus Type 1 Defective Viral Vector, Molecular & Cellular Neurosciences 2, 320–330 (1991).

Samulski et al., Helper–Free Stocks of Recombinant Adeno–Associated Viruses: Normal Integration Does Not Require Viral Gene Expression, Journal of Virology 63(9), 3822–3828 (1989).

Beard et al., Transcription Mapping of Mouse Adenovirus Type 1 Early Region 3, Virology 175, 81–90 (1990).

Levrero et al., Defective and nondefective adenovirus vectors for expressing foreign genes in vitro and in vivo, Gene 101, 195–202 (1991).

Graham, Covalently closed circles of humand adenovirus DNA are infectious, The EMBO Journal 3(12), 2917–2922 (1984).

Pinkert et al., An albumin enhancer located 10 kb upstream functions along with its promoter to direct efficient, liver–specific expression in transgenic mice, Genes & Development 1, 268–276 (1987).

Adams et al., The c–myc oncogene driven by immunoglobulin enhancers induces lymphoid malignancy in transgenic mice, Nature 318, 533–538 (1985).

Kelsey et al., Species– and tissue–specific expression of human alpha1–antitrypsin in transgenic mice Genes & Development 1, 161–171 (1987).

Johnson et al., Inhibition of Angiogenesis by Tissue Inhibitor of Metalloproteinase, Journal of Cellular Physiology 160, 194–202 (1994).

Wilhelm et al., Recombinant soluble urokinase receptor as a scavenger for urokinase–type plasminogen activator (uPA) Inhibition of proliferation and invasion of human ovarian cancer cells, FEBS Letters 337, 131–134 (1994).

Hutchinson et al., Mutagenesis at a Specific Position in a DNA Sequence, The Journal of Biological Chemistry 253(18), 6551–6560 (1978).

Oliphant et al., Cloning of random–sequence oligodeoxynucleotides, Gene 44, 177–183 (1986).

Bernstein et al., Gene Transfer with Retrovirus Vectors, Genetic Engineering 7, 235–261 (1985).

McCormick, Human Gene Therapy: The First Round, Bio/Technology 3(8), 689–693 (1985).

Miller et al., Improved Retroviral Vectors for Gene Transfer and Expression, Bio Techniques 7(9), 980–990 (1989).

Felgner et al., Cationic liposome–mediated transfection, Nature 337, 387–388 (1989).

Curiel et al., High–Efficiency Gene Transfer Mediated by Adenovirus Coupled to DNA–Polylysine Complexes, Human Gene Therapy 3, 147–154 (1992).

Zoller et al., Laboratory Methods—Oligonucleotide–Directed Mutagenesis: A Simple Method Using Two Oligonucleotide Primers and a Single–Stranded DNA Template, DNA 3(6), 479–488 (1984).

MacDonald, Expression of the Pancreatic Elastase I Gene in Transgenic Mice, Hepatology 7(1), 42S–51S (1987).

O'Reilly et al., Angiostatin: A Novel Angiogenesis Inhibitor That Mediates the Suppression of Metastases by a Lewis Lung Carcinoma, Cell 79, 315–328 (1994).

Dedieu et al., Long–Term Gene Delivery into the Livers of Immunocompetent Mice with E1/E4–Defective Adenovirus, Journal of Virology 71(6), 4626–4637 (1997).

Mirshahi et al., A monoclonal antibody directed against an epitope in the NH2–terminal region of native human plasminogen induced a modification of its functional properties, Fibrinolysis & Proteolysis 11(3), 155–163 (1997).

Farrell, Recombinant Herpesviruses Lacking Gene For Glycoprotein L, RD#37105A by Cantab Pharmaceuticals Res. Ltd (1995).

Palmer, Gyorffy, et al. "Combined treatment of a murine breast cancer model with type 5 adenovirus vectors expressing murine angiostatin and il–12: a role for combined anit–angiogenesis and immunotherapy," J. Immunol., May 15, 2001, 166(10):6212–7. (Abstract only).

Pili, R., et al. "Adenovirus–mediated gene transfer of fibroblast growth factor–1: angiogenesis and tumorigenicity in nude mice," Int. J. Cancer, Oct. 9, 1997, 73(2):258–63. (Abstract only).

Matsumoto, G., et al. "Angiostatin gene therapy inhibits the growth of murine squamous cell carcinoma in vivo," *Oral Oncol,* Jun. 2001, 37(4):369–78. (Abstract only).

Riccioni, T., et al. "Adenovirus–mediated wild–type p53 overexpression inhibits endothelial cell differentiation in vitro and angiogenesis in vivo," *Gene Ther,* Jun. 1998, 5(6):747–54. (Abstract only).

GenBank entry for human plasminogen and annotations from NCBI web page, Acc. No. P00747.

GenBank entry for human urokinase–type plasminogen activator and annotations from NCBI, Acc. No. P00749.

Abstract #1171 of an article by FUJIWARA et al., titled "Antiangiogenic therapy for human lung cancer by wild–type p53–mediated downregulation of vascular endothelial growth factor (VEGF) expression," Pharmacology/Therapeutics (Preclinical and Clinical) 12, p. 175.

* cited by examiner

ADENOVIRUS-MEDIATED INTRATUMORAL DELIVERY OF AN ANGIOGENESIS ANTAGONIST FOR THE TREATMENT OF TUMORS

This application claims full benefit of prior applications PCT/EP98/02491 and U.S. provisional application No. 60/044,980 filed on Apr. 28, 1997.

FIELD OF THE INVENTION

The present invention relates to gene therapy for the treatment of tumors. The invention more particularly relates to introduction of a gene encoding an anti-angiogenic factor into cells of a tumor, for example with an adenovirus vector, to inhibit growth or metastasis, or both, of the tumor.

BACKGROUND OF THE INVENTION

Cell migration is a coordinated process that bridges cellular activation and adhesion whereas the equilibrium between pericellular proteolysis and its inhibition (e.g., triggered by plasminogen activator inhibitors and tissue inhibitors of metalloproteinases) is disrupted (1–3). Urokinase plasminogen activator (uPA) is a pivotal player in this process because it initiates a proteolytic cascade at the surface of migrating cells by binding to its cell surface receptor (uPAR) (4, 5). Binding of uPA to its receptor greatly potentiates plasminogen/plasmin conversion at the cell surface (6). Plasmin is a broadly specific serine protease which can directly degrade components of the extracellular matrix such as fibronectin, vitronectin or laminin. Plasmin also indirectly promotes a localized degradation of the stroma by converting inactive zymogens into active metalloproteinases (7). The selective distribution of uPAR at the leading edge of migrating cells (invadopodes) apparently concentrates uPA secreted by themselves or by neighboring stroma cells (8). uPAR is also directly involved in cellular adhesion to the extracellular matrix as illustrated by its uPA-dependent binding to vitronectin (9), and because uPAR modulates the binding properties of several integrin molecules (10). Finally, uPA and plasmin are somehow involved in cell morphogenesis by activating or inducing the release of morphogenic factors such as vascular endothelial growth factor (VEGF), hepatocyte growth factor (HGF), fibroblast growth factors (FGFs) and transforming growth factor β (TGFβ) (11, 12).

Taken together, these observations indicate that the uPA/uPAR system controls cell migration by coordinating cellular activation, adhesion and motility. This statement is supported by clinical observations that correlate the presence of enhanced uPA activity at the invasive edge of the tumors (13, 14). That melanoma induced by DMBA and croton oil do not progress to a malignant stage in uPA-deficient mice also support a role of uPA in tumor establishment and progression (15).

uPA binds to uPAR by its light chain fragment, also known as amino-terminal fragment (ATF, amino acid 1–135). This interaction is species restricted (16) and involves the EGF-like domain of ATF (residues 1–46), in which amino acid 19–32, which are not conserved between mice and human, are critical (17, 18). ATF-mediated disruption of the uPA/uPAR complex inhibits tumor cell migration and invasion in vitro (19). Intraperitoneal bolus injection of a chimeric human ATF-based antagonist has also been used to inhibit lung metastases of human tumor cells implanted within athymic mice, without significantly affecting primary tumor growth (20). A further study reported that intraperitoneal injection of synthetic peptides derived from murine ATF was effective in inhibiting both primary tumor growth and lung metastases (21). These results are consistent with a role of the uPA/uPAR complex in controlling the motility of both tumor and endothelial cells (22). That a chimeric murine ATF-based antagonist could inhibit vessel growth in an artificial bFGF-enriched extracellular matrix (23) further supports uPA/uPAR involvement in controlling angiogenesis in vivo.

The formation of blood vessels, or angiogenesis, results from the capillary growth of pre-existing vessels. Angiogenesis is essential for a number of physiological processes such as embryonic development, wound healing and tissue or organ regeneration. Abnormal growth of new blood vessels occurs in pathological conditions such as diabetic retinopathy and tumor growth, as well as tumor dissemination to distant sites [38,24]. Both experimental and clinical studies have showed that primary tumors as well as metastasis remain dormant due to a balanced rate of proliferation and apoptosis unless the angiogenesis process is switched on [39].

The growth of endothelial cells is tightly regulated by both positive and negative factors. The onset of tumor angiogenesis could be triggered either by an upregulation of tumor-released angiogenic factors such as vascular endothelial growth factor (VEGF) and acid or/and basic fibroblast growth factor (bFGFs), or by a downregulation of angiostatic factors such as thrombospondin and angiostatin [39]. Both the reconstitution of angiostatic factors and the removal of angiogenic stimulating factors thus constitute plausible clinical strategies to suppress tumor angiogenesis [40, 41]. Angiostatic-based therapies should also apply to all solid tumors because endothelial cells do not vary from one tumor type to the other, further emphasizing the clinical relevance of such an anti-cancer approach. Thus, the therapy targeting angiogenesis appears to be highly relevant to clinical practice.

Many physiological angiostatic factors are derived upon proteolytic cleavage of circulating proteins. This is the case for angiostatin [32], endostatin [42], the 16 kDa fragment of prolactin [43], or platelet factor-4 [44]. Angiostatin was initially isolated from mice bearing a Lewis lung carcinoma (LLC), and was identified as a 38 kDa internal fragment of plasminogen (Plg) (aa 98–440) that encompasses the first four kringles of the molecule [32; WO95/29242; U.S. Pat. No. 5,639,725]. Angiostatin has been shown to be generated following hydrolysis of Plg by a metalloelastase from GM-CSF-stimulated tumor-infiltrating macrophages [45]. Intraperitoneal bolus injections of purified angiostatin in six different tumor models have proved to be very effective in suppressing primary tumor growth, with no apparent toxicity [46]. Angiostatin-mediated suppression of tumor angiogenesis apparently drove the tumor cells into a higher apoptotic rate that counterbalanced their proliferation rate. In this study, tumor growth usually resumed following removal of the angiostatin molecule, emphasizing the importance of achieving long-term delivery for optimal clinical benefits [46]. In vitro studies with recombinant proteins indicated that the angiostatic activity of angiostatin was mostly mediated by kringles 1–3, thus leaving a minor activity for kringle 4 [47]. As for most angiostatic factors, little is known about the molecular pathway by which angiostatin exerts its effect.

As angiostatic therapy will require a prolonged maintenance of therapeutic levels in vivo, the continuous delivery of a recombinant protein will be expensive and cumbersome. Direct in vivo delivery of the corresponding genes with viral vectors constitutes an attractive solution to this problem. Because most cancer gene therapies currently rely on destructive strategies that target the tumor cells [48], viral-mediated gene delivery of an angiostatic factor represents a conceptually different, and possibly synergistic, approach to fight cancer.

Despite these results, there remains a need to develop effective treatments for tumors, particularly chemotherapy-resistant tumors.

The present invention addresses this need by establishing an effective mode for treating a tumor.

Various references are cited in this specification by number, which are fully set forth after the Examples. None of the references cited herein should be construed as describing or suggesting the invention disclosed herein.

SUMMARY OF THE INVENTION

The present invention advantageously provides a highly effective gene therapy for tumors. Indeed, in a specific embodiment of the invention murine urokinase ATF expressed by human tumor cells in an athymic murine model unexpectedly effectively inhibits tumorigenicity. In another embodiment, angiostatin expressed in tumor cells in a murine model inhibited tumor growth and tumorigenesis, and induced tumor cell apoptosis, in addition to blocking angiogenesis.

In a broad aspect, the present invention provides a method for inhibiting growth or metastasis, or both, of a tumor comprising introducing a vector comprising a gene encoding an anti-angiogenic factor operably associated with an expression control sequence that provides for expression of the anti-angiogenic factor into a cell or cells of the tumor. Preferably, the vector is a virus vector; more preferably the virus vector is an adenovirus vector. In a specific embodiment exemplified infra, the adenovirus vector is a defective adenovirus vector.

The methods of the invention are useful in the treatment of many tumors, as set forth in detail herein. For example, in specific embodiments, the tumor is a lung carcinoma or a breast carcinoma.

In addition, the invention demonstrates for the first time the advantages of expression of an anti-angiogenic factor by the transduced tumor cells. Accordingly, a gene encoding any anti-angiogenic factor, such as a soluble receptor for an angiogenic protein, or an angiogenesis antagonist, can be delivered in the practice of the invention. In a specific embodiment, the anti-angiogenic factor comprises a sequence of an amino terminal fragment of urokinase having an EGF-like domain, with the proviso that the factor is not urokinase. For example, the anti-angiogenic factor may be a chimeric protein comprising ATF-immunoglobulin or ATF-human serum albumin. In a preferred embodiment, exemplified infra, the anti-angiogenic factor is an amino terminal fragment of urokinase having an amino acid sequence of urokinase from about amino acid residue 1 to about residue 135. In a specific aspect, the urokinase is murine urokinase. In a more preferred aspect, the urokinase is human urokinase.

In an alternative embodiment, the anti-angiogenic factor is angiostatin, in particular, kringles 1 to 3 of angiostatin. In a particularly preferred embodiment, the anti-angiogenic factor is the amino-terminal fragment of plasminogen (Plg) having an amino acid sequence of plasminogen from about amino acid residue 1 to about residue 333. In another preferred embodiment, the anti-angiogenic factor is the amino-terminal fragment (angiostatin) from human plasminogen.

In a related embodiment, the invention is directed to use of a vector comprising a gene encoding an anti-angiogenic factor operably associated with an expression control sequence that provides for expression of the anti-angiogenic factor in the manufacture of a medicament for inhibiting growth or metastasis, or both, of a tumor. More particularly, the invention provides for use of a virus vector of the invention, e.g., as set out below, in the manufacture of a medicament for inhibiting growth or metastasis, or both, of a tumor.

Naturally, in addition to the foregoing methods and uses, the invention provides a novel virus vector comprising a gene encoding an anti-angiogenic factor operably associated with an expression control sequence. In a preferred embodiment, the virus vector is an adenovirus vector. In a more preferred embodiment, the virus vector is a defective adenovirus vector. The virus vectors of the invention can provide a gene encoding any anti-angiogenic factor, as set forth above. For example, the anti-angiogenic factor may comprise a sequence of an amino terminal fragment of urokinase having an EGF-like domain, with the proviso that the factor is not urokinase. In a preferred embodiment, the anti-angiogenic factor is an amino terminal fragment of urokinase having an amino acid sequence of urokinase from amino acid residue 1 to about residue 135. In this embodiment, the urokinase may be murine urokinase or, preferably, human urokinase.

The invention further provides a pharmaceutical composition any of the virus vectors of the invention and a pharmaceutically acceptable carrier.

Thus, one object of the invention is to provide gene therapy by delivery of anti-angiogenic factors for treating tumors.

Another object of the invention is to provide a viral vector for delivery of an anti-tumorigenic factor.

Still another object of the invention is to provide an amino terminal fragment of urokinase (ATF) by gene therapy for treatment of a tumor.

Further, another object of the invention is to provide angiostatin by gene therapy for treatment of a tumor.

Yet another object of the invention is to provide angiostatin, particularly kringles 1 to 3 of angiostatin, by gene therapy for treatment of a tumor.

These and other objects of the invention are further elaborated in the following Detailed Description and Examples, and the accompanying drawings.

The culture media of mock-infected cells (lane 1), or infected with AdCO1 (lane 2) or AdmATF (lane 3) were submitted to a western blot analysis with a polyclonal anti-mouse uPA antibody.

Figure 2:
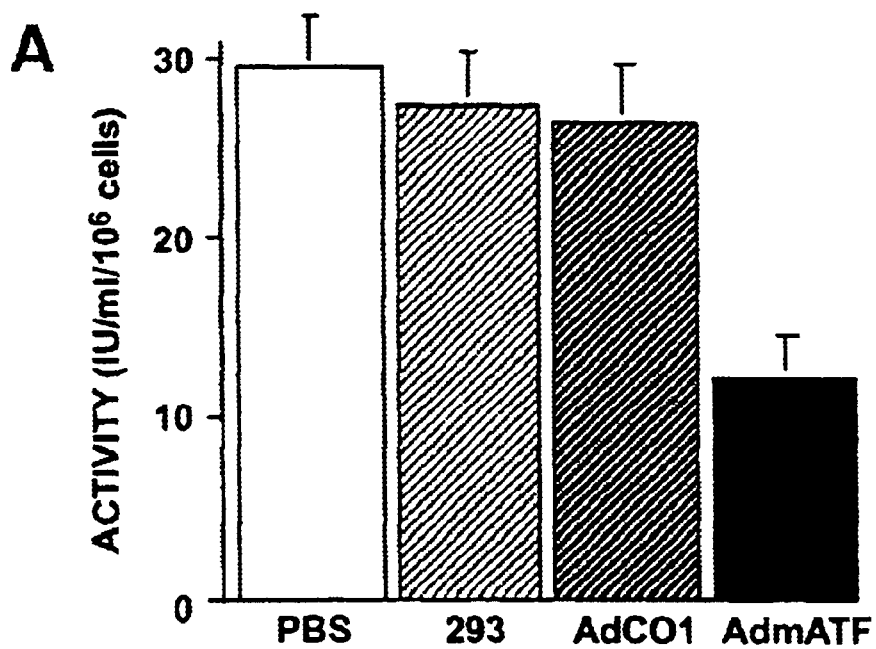
Figure 2:
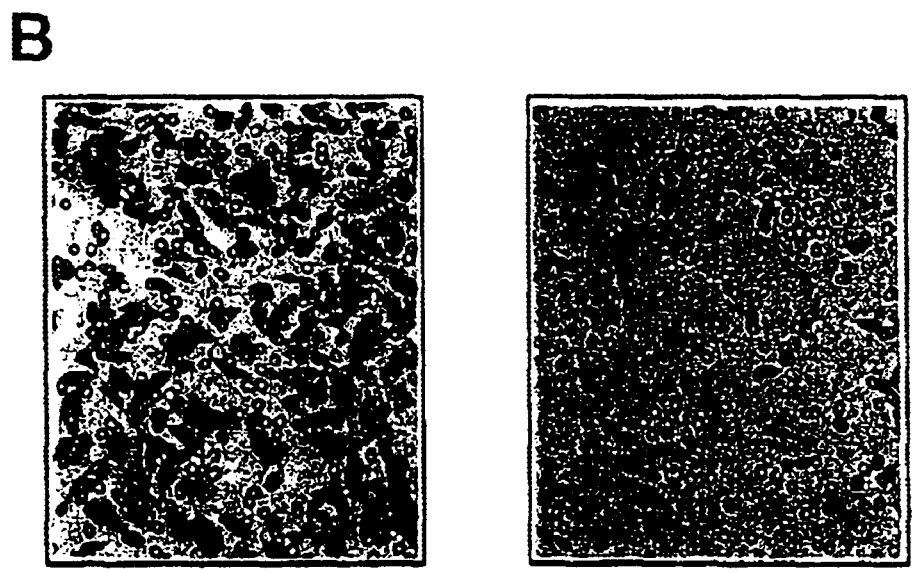

FIG. 2. Functional characterization of virus AdmATF. Panel A: The culture medium of AdmATF-infected cells inhibits plasmin conversion at the surface of LLC cells (see Methods section of the Example). 293 refers to the supernatant of non infected cells. Panel B: Infection of LLC cells with AdmATF (right panel) specifically inhibits cell invasiveness as compared to that of LLC cells infected with AdCO1 (left panel). The 1.2 mm pores of the membranes are visible.

Figure 3:
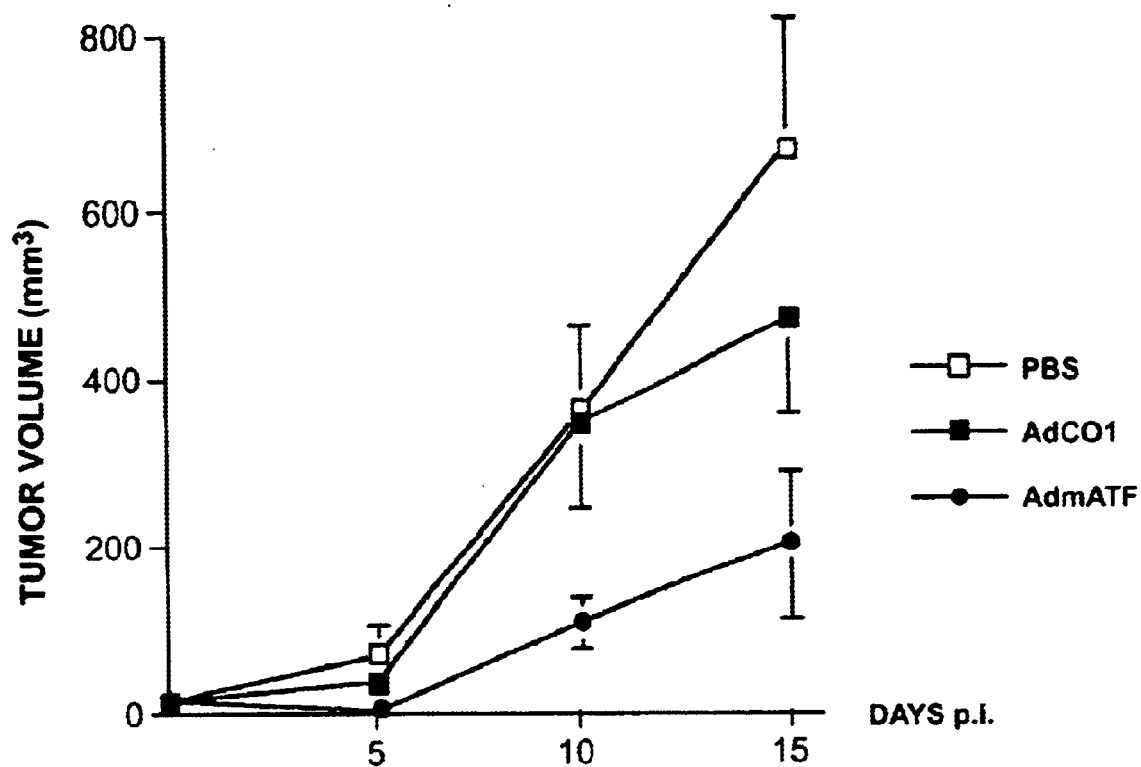

FIG. 3. Intratumoral injection of AdmATF inhibits LLC tumor growth in syngeneic mice. Tumor cells ($2\times10^6$ cells) were subcutaneously injected into C57BL/6 mice. After 6 days, the animals received an intratumoral injection of PBS, or $10^9$ PFU of AdCO1 or AdmATF and tumor growth was monitored. The mean values are represented with their standard variations (n=10). Statistics were done with the Student test.

Figure 4:
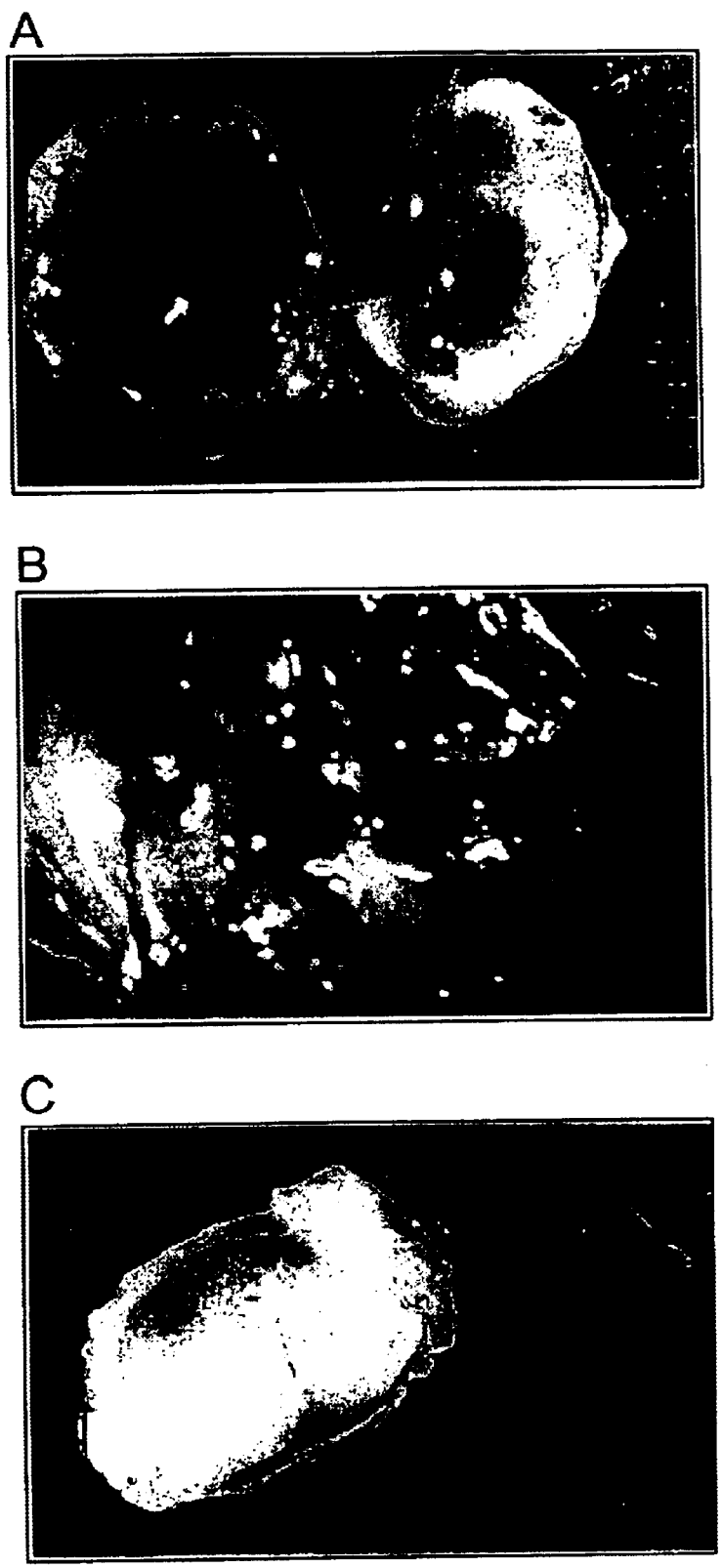

FIG. 4. Intratumoral injection of AdmATF inhibits LLC tumor vascularization. Panel A: a representative tumor from the AdCO1-treated (left) and AdmATF-treated groups extracted at day 10 p.i. is shown. A representative tumor extracted at day 20 p.i. is shown in panel B (injection with AdCO1) and panel C (injection with AdmATF). All photographs were taken at the same magnification. Note that the AdmATF-injected tumors are much smaller that their AdCO1-injected controls, especially at the latest time p.i. (compare panels B and C).

Figure 5:
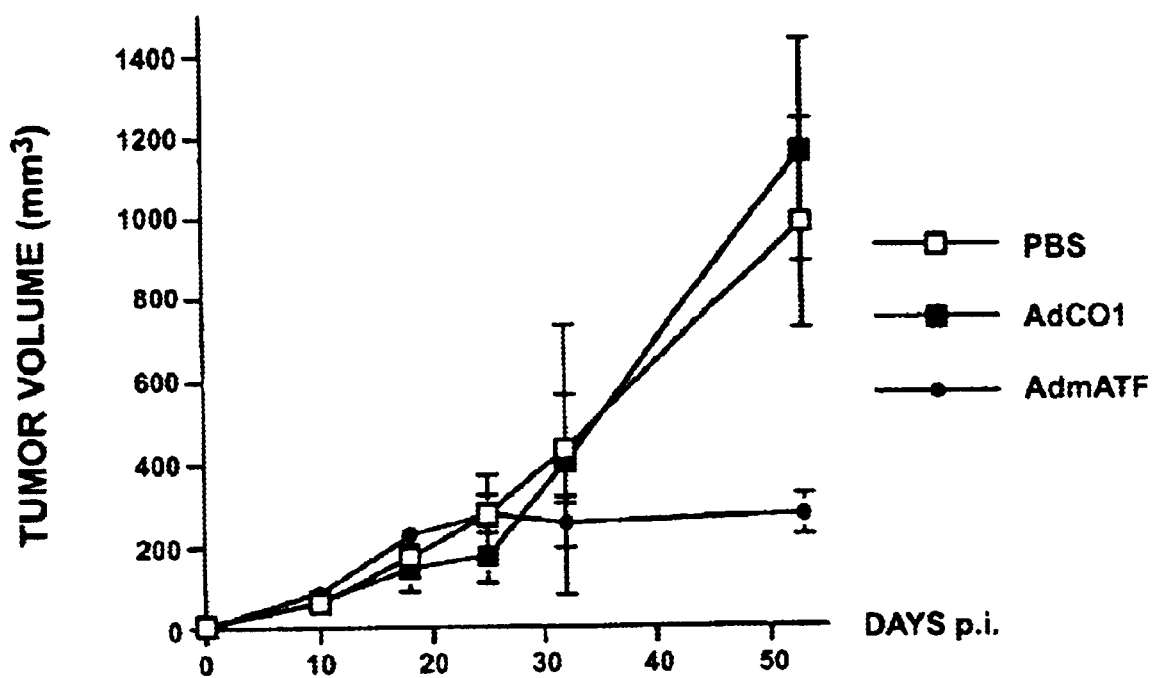

FIG. 5. Intratumoral injection of AdmATF inhibits MDA-MB-231 tumor growth in nude mice. Tumors were implanted by subcutaneous injection of $3\times10^6$ MDA-MB-231 cells. At day 11 post implantation, the mice received an intratumoral injection of PBS, or $10^9$ PFU of AdmATF or AdCO1, and the tumor growth was monitored. The mean values are represented with their standard variations.

Figure 6:
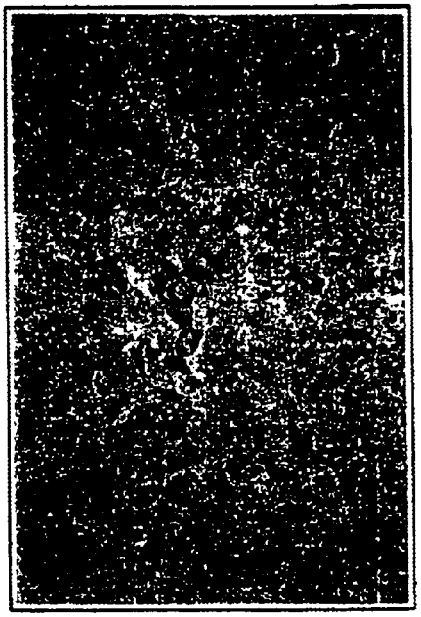
Figure 6:
Figure 6:
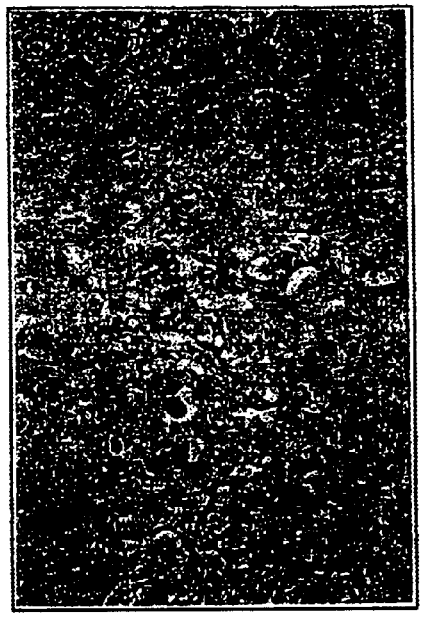
Figure 6:

FIG. 6. Intratumoral injection of AdmATF inhibits intratumoral and peritumoral angiogenesis. Panels A and B: vWF immunostaining of tumor sections. Paraffin embedded MDA-MB-231 tumor sections prepared from the AdCO1- (A) and AdmATF-treated groups (B) were revealed with a polyclonal anti-vWF serum at day 52 p.i. Panels C and D: Macroscopic evaluation of peritumoral vascularization within the skin of tumors injected with AdCO1 (C) or AdmATF (D) at day 20 p.i.

Figure 7:
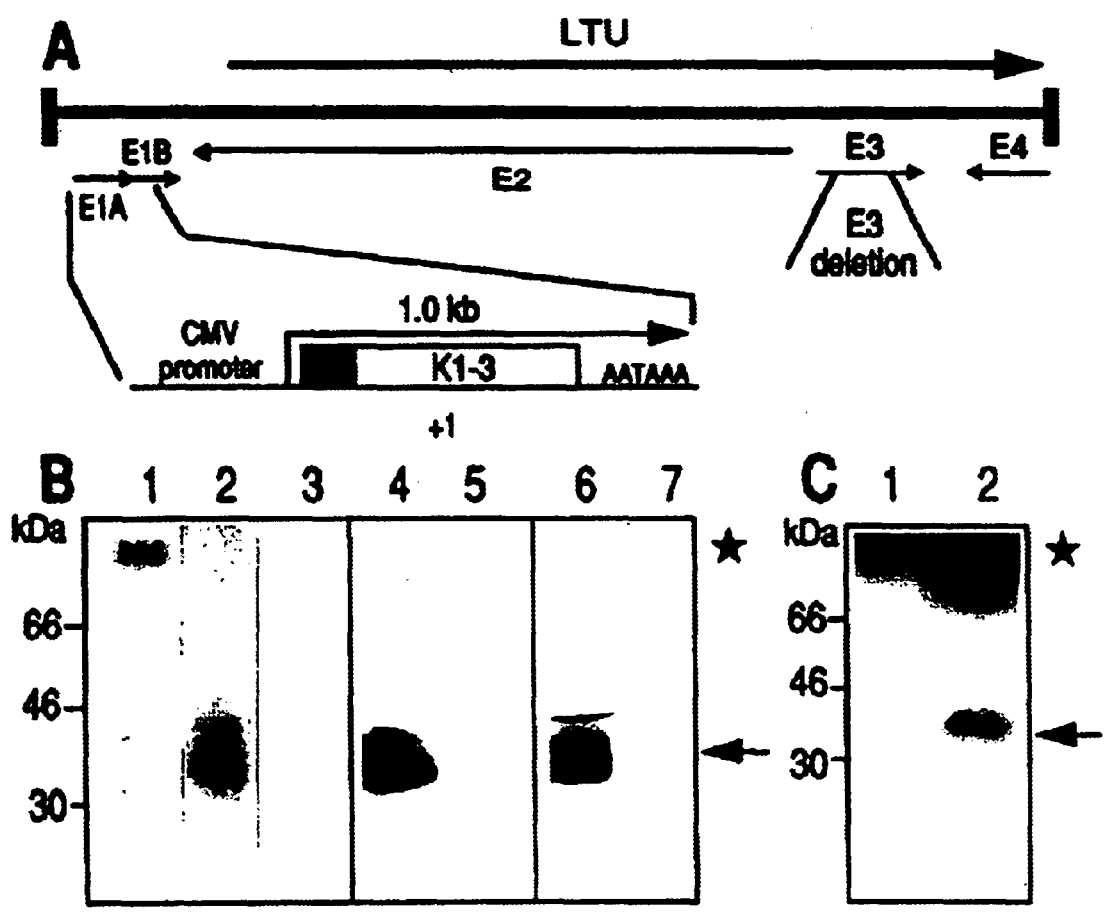

FIG. 7. (A) Recombinant adenoviruses. The Ad5 genome is a 36 kb-long chromosome. Viruses AdK3 and AdCO1 were derived by a lethal deletion of the E1 genes (nucleotide position 382 to 3446); they also carry a non-lethal 1.9 kb XbaI deletion within region E3 (for a review see [37]). The angiostatin expression cassette is shown under the Ad5 chromosome. The plasminogen secretion signal is represented by a blackened box; +1 refers to the CMV-driven transcription start; AATAAA refers to the SV40 late polyadenylation signal. (B) Analysis of angiostatin secretion from infected-cells. 100 ng of human Plg (lane 1), culture medium from HMEC-1 infected with AdK3 (lane 2) or AdCO1 (lane 3), C6 infected with AdK3 (lane 4) or AdCO1 (lane 5), and from MDA-MB-231 infected with AdK3 (lane 6) or AdCO1 (lane 7) were submitted to Western blot analysis. (C) Immuno-detection of angiostatin within C6 tumor extracts; Tumors were established in nude mice and received $10^9$ PFU of AdCO1 (lane 1) or AdK3 (lane 2) and Western blot analysis was performed 10 days p.i. The signal corresponding to angiostatin (36–38 kDa) and Plg (92 kDa) are indicated (arrow and asterisk respectively).

Figure 8:
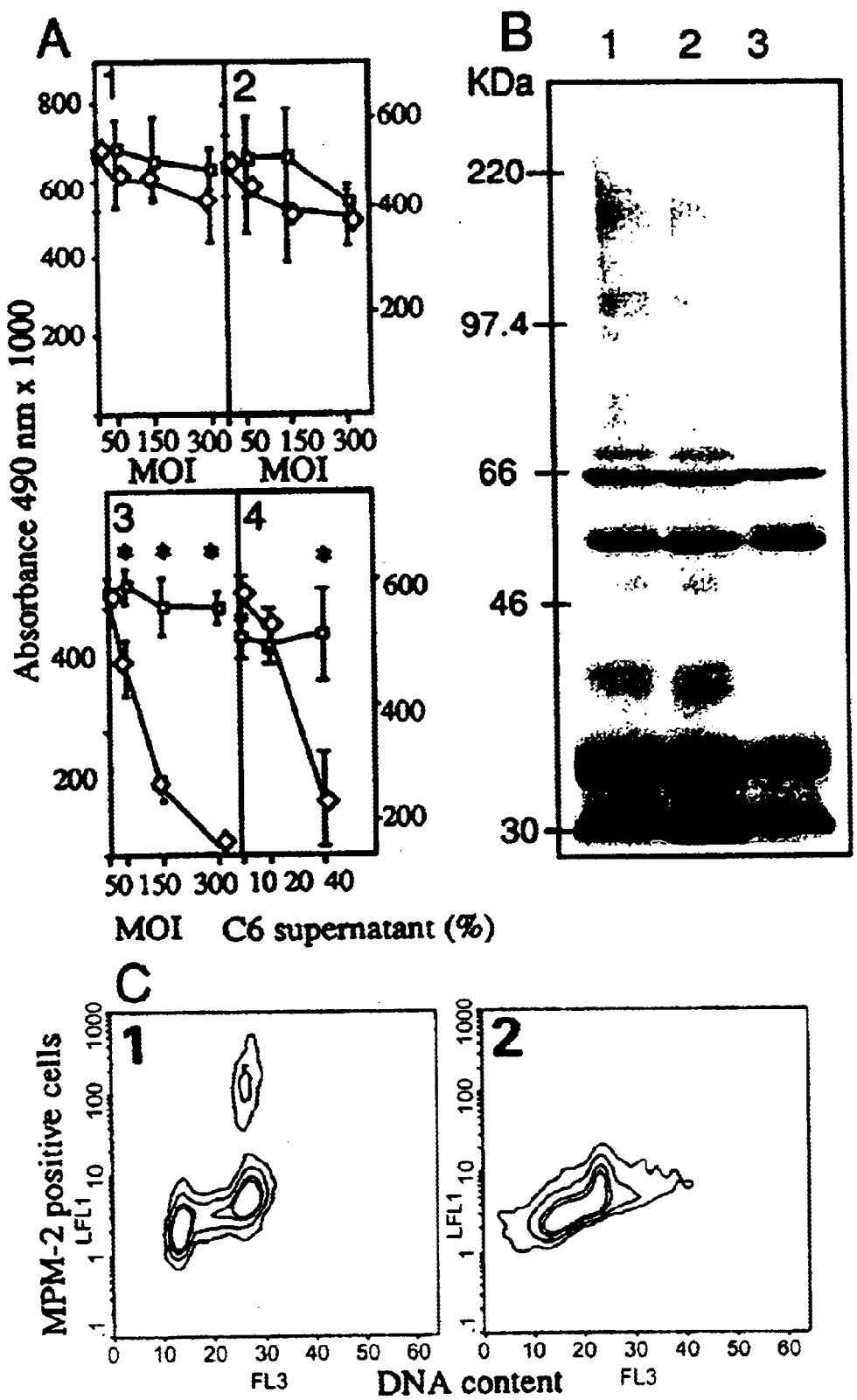

FIG. 8. (A) Inhibition of endothelial cell proliferation. C6 (panel 1), MDA-MB-231 (panel 2) and HMEC-1 (panel 3) were injected with AdK3 (♦) or Ad-CO1 (□). HMEC-1 cells (panel 4) cultured with the supernatant from AdK3-(♦) or AdCO1-infected C6 glioma cells (□). (B) Detection of MPM-2 phosphoepitope in HMEC-1 cells. Mock-infected cells (lane 1), AdCO1-infected cells (lane 2), and AdK3-infected cells (lane 3). (C) MPM-2 epitope were detected in HMEC-1 infected with AdCO1 (panel 1) or AdK3 (panel 2) by indirect immunostaining and DNA content by propidium iodide staining, and quantified by flow cytometry (see Methods). A Student's t-test was used for statistical analysis.

Figure 9:
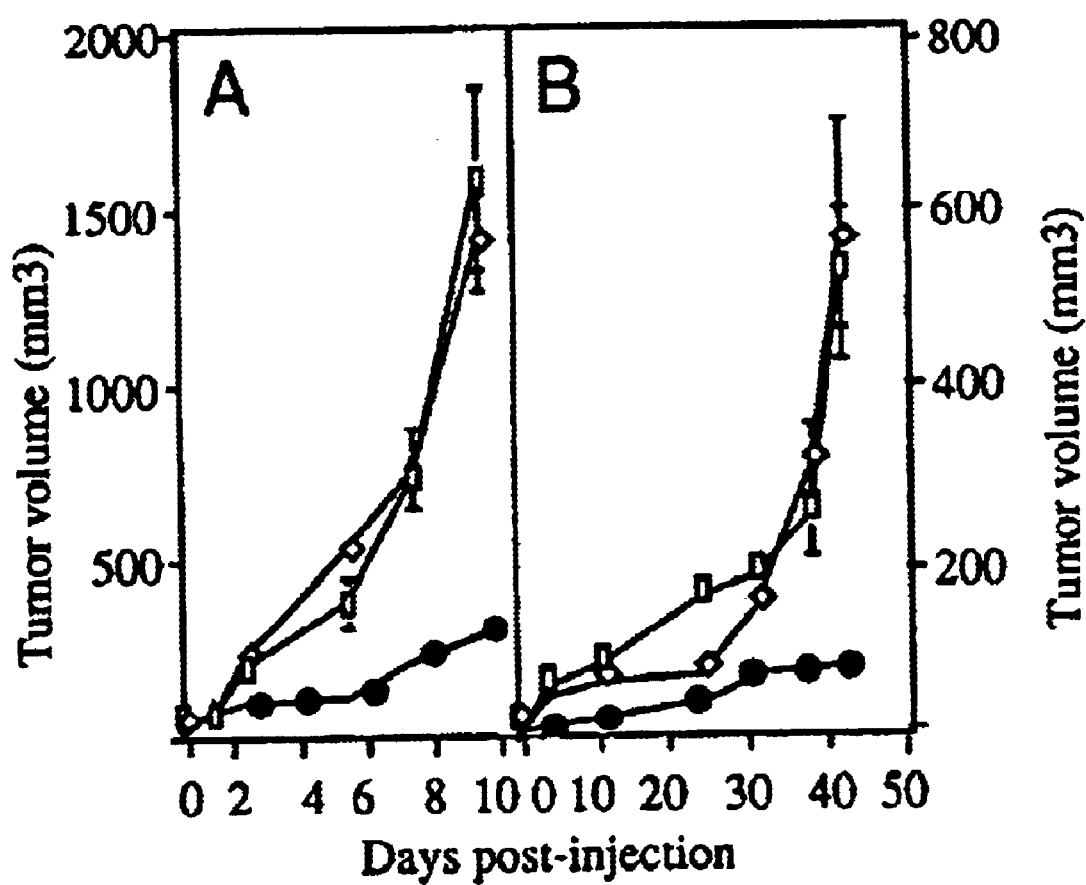

FIG. 9. AdK3 inhibits tumor growth. C6 glioma (panel A) and MDA-MB-231 carcinoma (panel B) were subcutaneously implanted into athymic mice (see Methods). When the tumor had reached a volume of 20 mm$^3$ (day 0), mice received an intratumoral injection of PBS (□), or $10^9$ PFU or AdK3 (●) or AdCO1 (♦). Mean values are represented with their standard deviations.

Figure 10:
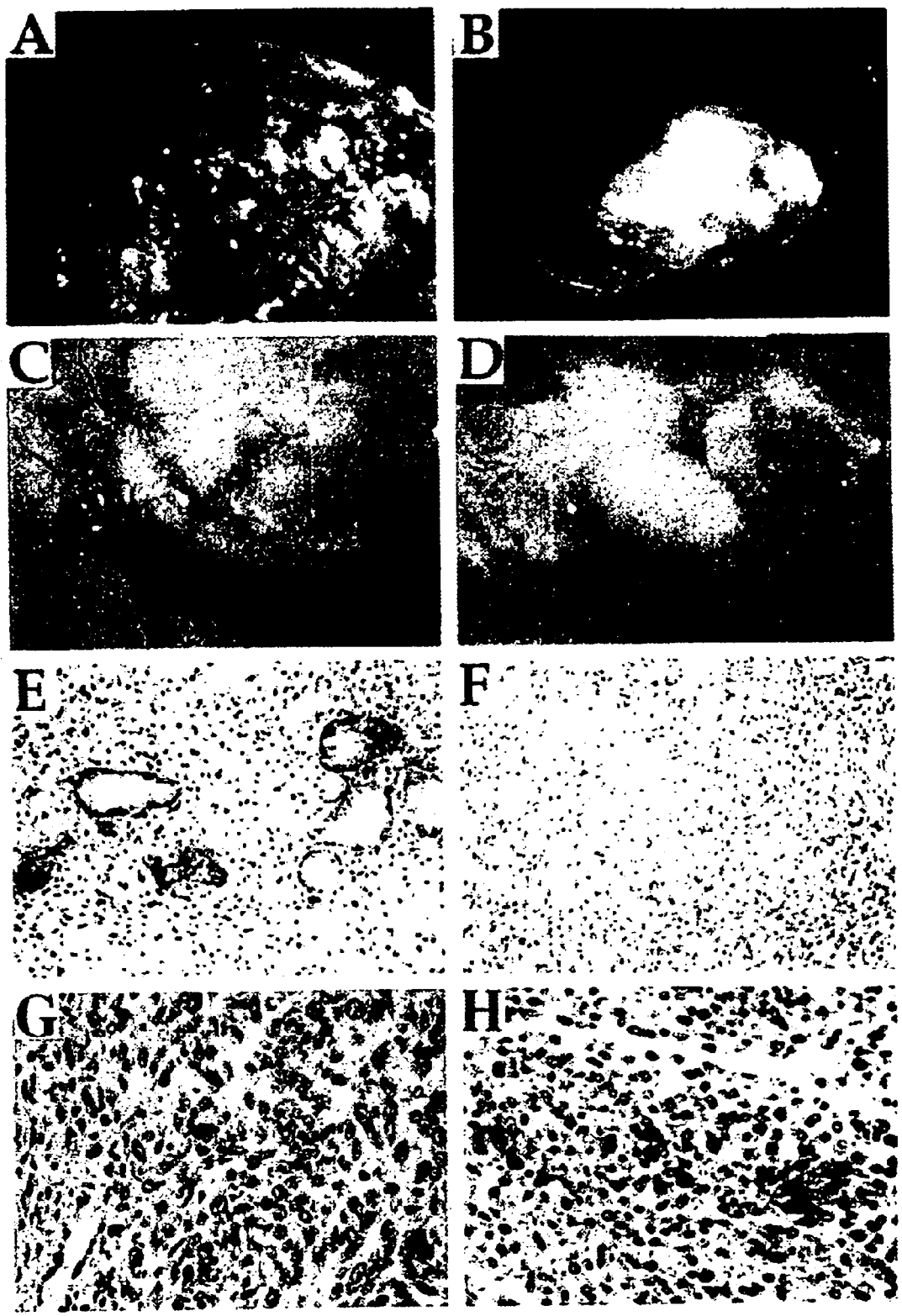

FIG. 10. AdK3 inhibits C6 tumor growth and angiogenesis. Tumors from AdCO1-treated (panel A) and AdK3-treated groups (panel B) are shown 10 days p.i. The extent of vascularization at the periphery of a representative tumor injected with AdCO1 (panel C) or AdK3 (panel D) is shown at day 5 p.i. Paraffin-embedded C6 sections from an AdCO1-injected (panel E) or an AdK3-injected tumor (panel F) were submitted to vWF-immunostaining at day 10 p.i. The proportion of apoptotic cells was detected by the TUNEL method within sections from an AdCO1-injected (panel G) or an AdK3-injected tumor (panel H). The same magnification was used for AdCO1- and AdK3-injected tumors.

Figure 11:
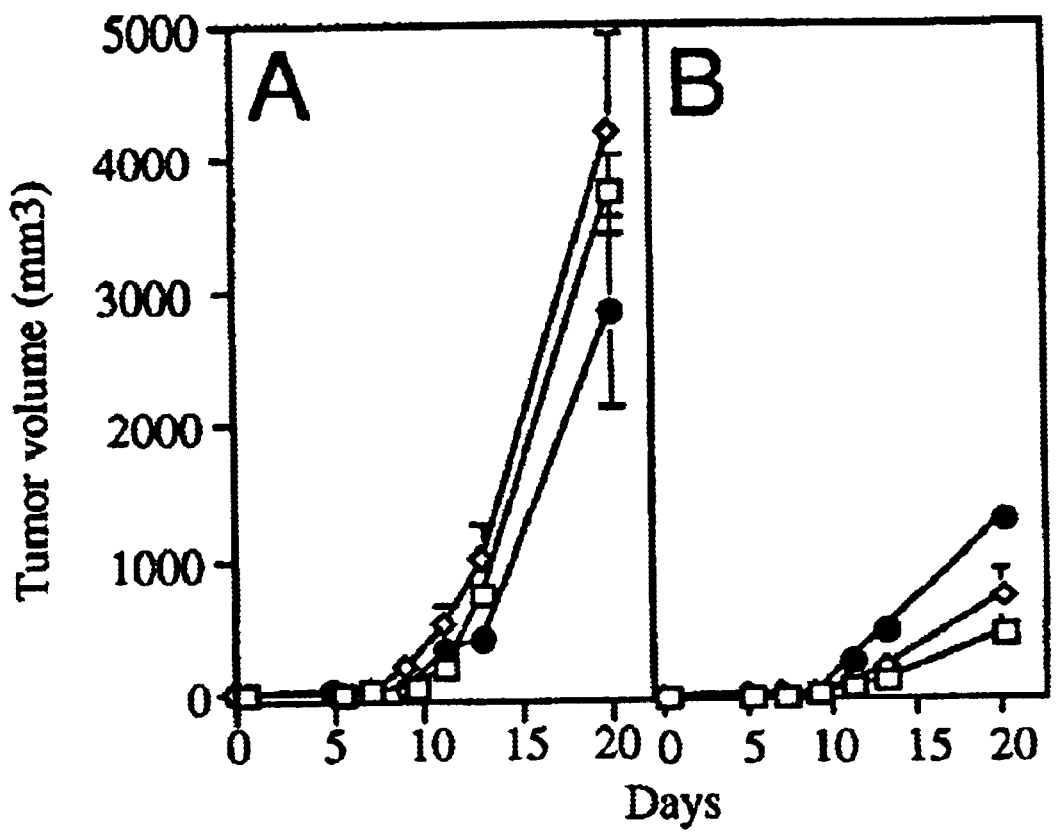

FIG. 11. Dose dependent effect of AdK3. C6 cells were infected in vitro, 24 hours with AdCO1 (panel A) or Ad3 K (panel B) and mixed with a ratio of 1 (□), 1:2 (♦) and 1:4 (●) with non-infected C6 cells, prior to C6 cells implantation into athymic mice. Tumor volumes were measured during 20 days. Mean values are represented with their standard deviations.

DETAILED DESCRIPTION OF THE INVENTION

As disclosed above, the present invention is directed to methods and vectors for gene therapy of tumors. The methods and vectors of the invention inhibit tumor growth or tumor metastasis, or both. These methods and vectors act by inhibiting angiogenesis of the tumor to an unexpectedly advantageous degree.

The invention is based, in part, on experiments involving gene therapy delivery of the amino terminal fragment of urokinase (ATF) and angiostatin. ATF is an antagonist of urokinase (uPA) binding to its cell surface receptor (uPAR), and an inhibitor of endothelial cell migration. To assess the importance of the uPA/uPAR interaction for tumor growth and dissemination, a defective adenovirus expressing murine ATF from the CMV promoter (AdmATF) was constructed. A single intratumoral injection of AdmATF inhibited growth of pre-established tumors in two different murine models, and delayed tumor dissemination. These effects were correlated with a remarkable inhibition of neovascularization within, and at the immediate vicinity of, the injection site. The magnitude of this effect was particularly remarkable in the ability of murine ATF to inhibit angiogenesis of a human-derived tumor. In a specific example, a defective adenovirus that expresses the N-terminal fragment (aa 1-333) from human Plg, including the pre-activation peptide and kringles 1 to 3 [47] was constructed (AdK3) and its in vitro and in vivo activity in different murine tumor models was assessed. The AdK3 vector inhibited tumor growth, tumor angiogenesis, and tumorigenesis, and induced tumor cell apoptosis.

Intratumoral adenovirus-mediated delivery of antagonist displays potent antitumoral properties by targeting angiogenesis.

Definitions

The following defined terms are used throughout the present specification, and should be helpful in understanding the scope and practice of the present invention.

In a specific embodiment, the term "about" or "approximately" means within. 20%, preferably within 10%, and more preferably within 5% of a given value or range.

An "anti-angiogenic" factor is a molecule that inhibits angiogenesis, particularly by blocking endothelial cell migration. Such factors include fragments of angiogenic proteins that are inhibitory (such as the ATF of urokinase), angiogenesis inhibitory factors, such as angiostatin and endostatin; and soluble receptors of angiogenic factors, such as the urokinase receptor or FGF/VEGF receptor. The term "angiostatin", which is derived from the amino-terminal fragment of plasinogen, includes the anti-angiogenic fragment of angiostatin having kringles 1 to 3. Generally, an anti-angiogenic factor for use in the invention is a protein or polypeptide encoded by a gene transfected into tumors using the vectors of the invention.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

General Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is any means for the transfer of a nucleic acid according to the invention into a host cell. The term "vector" includes both viral and nonviral means for introducing the nucleic acid into a cell in vitro, ex vivo or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors, as set forth in greater detail below. In addition to a nucleic acid according to the invention, a vector may also contain one or more regulatory regions, and/or selectable markers useful in selecting, measuring, and monitoring nucleic acid transfer results (transfer to which tissues, duration of expression, etc.).

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" or "transduced" by exogenous or heterologous DNA when the transfected DNA effects a phenotypic change.

"Heterologous" DNA refers to DNA not naturally located in the cell, or in a chromosomal site of the cell. Preferably, the heterologous DNA includes a gene foreign to the cell.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides or nucleic acid sequence that encodes a protein is called the sense sequence. A "recombinant DNA molecule" is a DNA molecule that has undergone a molecular biological manipulation.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then optionally trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "corresponding to" is used herein to refer similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The various aspects of the invention will be set forth in greater detail in the following sections, directed to suitable gene therapy vectors and promoters, anti-angiogenic proteins, and therapeutic strategies. This organization into various sections is intended to facilitate understanding of the invention, and is in no way intended to be limiting thereof.

Gene Therapy Vectors

As discussed above, a "vector" is any means for the transfer of a nucleic acid according to the invention into a host cell. Preferred vectors are viral vectors, such as retroviruses, herpes viruses, adenoviruses and adeno-associated viruses. Thus, a gene or nucleic acid sequence encoding an anti-angiogenic protein or polypeptide domain fragment thereof is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Viral vectors commonly used for in vivo or ex vivo targeting and therapy procedures are DNA-based vectors and retroviral vectors. Methods for constructing and using viral vectors are known in the art [see, e.g., Miller and Rosman, BioTechniques 7:980–990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillomavirus, Epstein-Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., Molec. Cell. Neurosci. 2:320–330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [J. Clin. Invest. 90:626–630 (1992); see also La Salle et al., Science 259:988–990 (1993)]; and a defective adeno-associated virus vector [Samulski et al., J. Virol. 61:3096–3101 (1987); Samulski et al., J. Virol. 63:3822–3828 (1989); Lebkowski et al., Mol. Cell. Biol. 8:3988–3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ(IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

Adenovirus vectors. In a preferred embodiment, the vector is an adenovirus vector. As shown in the Examples, defective adenovirus vectors have shown themselves to be particularly effective for delivery of the angiogenesis inhibitors ATF and angiostatin, as shown by the unexpectedly efficient effects of inhibiting tumor growth and tumorigenesis. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g., Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-associated viruses. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

The invention also relates, therefore, to an AAV-derived recombinant virus whose genome encompasses a sequence encoding a nucleic acid encoding an anti-angiogenic factor flanked by the AAV ITRs. The invention also relates to a plasmid encompassing a sequence encoding a nucleic acid encoding an anti-angiogenic factor flanked by two ITRs from an AAV. Such a plasmid can be used as it is for transferring the nucleic acid sequence, with the plasmid, where appropriate, being incorporated into a liposomal vector (pseudo-virus).

Retrovirus vectors. In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et al., 1993, Blood 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. 61 (1987) 1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Targeted gene delivery is described in International Patent Publication WO 95/28494, published October 1995.

Non-viral Vectors. Alternatively, the vector can be introduced in vivo as nucleic acid free of transfecting excipients, or with transfection facilitating agents, e.g., lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Feigner, et. al., Proc. Natl. Acad. Sci. U.S.A. 84:7413–7417 (1987); see Mackey, et al., Proc. Natl Acad. Sci. U.S.A. 85:8027–8031 (1988); Ulmer et al., Science 259:1745–1748 (1993)]. The use of cationic lipids may promote encapsulation of negatively charged nucleic acids, and also promote fusion with negatively charged cell membranes [Feigner and Ringold, Science 337:387–388 (1989)]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/2193 1), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267:963–967 (1992); Wu and Wu, J. Biol. Chem. 263:14621–14624 (1988); Hartmut et al., Canadian Patent Application No. 2,012,311, filed Mar. 15, 1990; Williams et al., Proc. Natl. Acad. Sci. USA 88:2726–2730 (1991)]. Receptor-mediated DNA delivery approaches can also be sued [Curiel et al., Hum. Gene Ther. 3:147–154(1992); Wu and Wu, J Biol. Chem. 262:4429–4432 (1987)].

The nucleic acid can also be administered as a naked DNA. Methods for formulating and administering naked DNA to mammalian muscle tissue are disclosed in U.S. Pat. No. 5,580,859 and 5,589,466, the contents of which are incorporated herein by reference.

Regulatory Regions. Expression of an anti-angiogenic factor from a vector of the invention may be controlled by any regulatory region, i.e., promoter/enhancer element known in the art, but these regulatory elements must be functional in the host target tumor selected for expression.

The regulatory regions may comprise a promoter region for functional transcription in the tumor, as well as a region situated in 3' of the gene of interest, and which specifies a signal for termination of transcription and a polyadenylation site. All these elements constitute an expression cassette.

Promoters that may be used in the present invention include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the E1A, MLP, CMV and RSV genes and the like.

In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted, such as into the virus genome downstream of such a sequence.

Some promoters useful for practice of this invention are ubiquitous promoters (e.g., HPRT, vimentin, actin, tubulin), intermediate filament promoters (e.g., desmin, neurofilaments, keratin, GFAP), therapeutic gene promoters (e.g., MDR type, CFTR, factor VIII), tissue-specific promoters (e.g., actin promoter in smooth muscle cells), promoters which are preferentially activated in dividing cells, promoters which respond to a stimulus (e.g., steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the contents of which are incorporated herein by reference.

Thus, the promoters which may be used to control gene expression include, but are not limited to, the cytomegalovirus (CMV) promoter, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the b-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Genes Encoding Anti-Angiogenic Proteins

The vectors of the invention can be used to deliver a gene encoding an anti-angiogenic protein into a tumor in accordance with the invention. In a preferred embodiment, the anti-angiogenic factor is the amino terminal fragment (ATF) of urokinase, containing the EGF-like domain. Such fragment corresponds to amino acid residues about 1 to about 135 of ATF.

In another embodiment, ATF may be provided as a fusion protein, e.g., with immunoglobulin or human serum albumin [WO93/15199], which is specifically incorporated herein by reference in its entirety.

An effective ATF for use in the invention can be derived from any urokinase, such as murine urokinase, although human urokinase ATF is preferred. In addition, the invention contemplates administration of a non-human urokinase ATF modified by substitution of specific amino acid residues with the corresponding residues from human ATF. For example, murine ATF can be modified at one or more, and preferably all, amino acid residues as follows: tyrosine-23 to asparagine; arginine-28 to asparagine; arginine-30 to histidine; and arginine-31 to tryptophan. Thus, urokinase ATF from any source can be humanized. This is easily accomplished by modifying the coding sequence using routine molecular biological techniques.

Genes encoding other anti-angiogenesis protein can also be used according to the invention. Such genes include, but are not limited to, genes encoding angiostatin [O'Reilly et al., Cell 79:315–328 (1994); WO95/29242; U.S. Pat. No. 5,639,725], including angiostatin comprising kringles 1 to 3; tissue inhibition of metalloproteinase [Johnson et al., J. Cell. Physiol. 160:194–202 (1994)]; inhibitors of FGF or VEGF; and endostatin [WO97/15666]. In a preferred embodiment, the anti-angiogenic factor is angiostatin, particularly kringles 1 to 3 of angiostatin. In a particularly preferred embodiment, the anti-angiogenic factor is the amino-terminal fragment of plasminogen (Plg) having an amino acid sequence of plasminogen from about amino acid residue 1 to about residue 333. In another preferred embodiment, the amino terminal fragment of plasminogen/angiostatin is human plasminogen (angiostatin).

In another embodiment, the invention provides for administration of genes encoding soluble forms of receptors for angiogenic factors, including but not limited to soluble VGF/VEGF receptor, and soluble urokinase receptor [Wilhem et al., FEBS Letters 337:131–134 (1994)].

In general, any gene encoding a protein or soluble receptor that antagonizes endothelial cell activation and migration, which is involved in angiogenesis, can be employed in the gene therapy vectors and methods of the invention. Notwithstanding, it is particularly noteworthy that gene therapy delivery of ATF or angiostatin is especially effective in this regard, for reasons pointed out above and exemplified below.

A gene encoding an anti-angiogenic factor, whether genomic DNA or cDNA, can be isolated from any source, particularly from a human cDNA or genomic library. Methods for obtaining such genes are well known in the art, as described above [see, e.g., Sambrook et al., 1989, supra].

Due to the degeneracy of nucleotide coding sequences, other nucleic acid sequences which encode substantially the same amino acid sequence as an anti-angiogenic factor gene may be used in the practice of the present invention and these are contemplated as falling within the scope of the claimed invention. These include but are not limited to allelic genes, homologous genes from other species, and nucleotide sequences comprising all or portions of anti-angiogenic factor genes which are altered by the substitution of different codons that encode the same amino acid residue within the sequence, thus producing a silent change. Likewise, the anti-angiogenic factor derivatives of the invention include, but are not limited to, those containing, as a primary amino acid sequence, all or part of the amino acid sequence of an anti-angiogenic factor protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

The genes encoding anti-angiogenic factor derivatives and analogs of the invention can be produced by various methods known in the art. The manipulations which result in their production can occur at the gene or protein level. For example, the cloned anti-angiogenic factor gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of anti-angiogenic factor, care should be taken to ensure that the modified gene remains within the same translational reading frame as the anti-angiogenic factor gene, uninterrupted by translational stop signals, in the gene region where the desired activity is encoded.

Additionally, the anti-angiogenic factor-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification, such as to form a chimeric gene. Preferably, such mutations enhance the functional activity of the mutated anti-angiogenic factor gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in PCR Technology: Principles and Applications for DNA Amplification, H. Erlich, ed., Stockton Press, Chapter 6, pp. 61–70).

Therapeutic Targets and Strategies

The process according to the present invention enables one to treat tumors. According to the present invention, it is now possible, by ajudicious choice of various injections, infusions, direct application, etc., to infect specifically and unilaterally a large number of tumor cells.

Pharmaceutical Compositions. For their use according to the present invention, the vectors, either in the form of a virus vector, nucleic acid-lipid composition, or naked DNA, are preferably combined with one or more pharmaceutically acceptable carriers for an injectable formulation. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, allow the constitution of injectable solutions.

The preferred sterile injectable preparations can be a solution or suspension in a nontoxic parenterally acceptable solvent or diluent. Examples of pharmaceutically acceptable carriers are saline, buffered saline, isotonic saline (e.g., monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The virus doses used for the administration may be adapted as a function of various parameters, and in particular as a function of the site (tumor) of administration considered, the number of injections, the gene to be expressed or alternatively the desired duration of treatment. In general, the recombinant adenoviruses according to the invention are formulated and administered in the form of doses of between $10^4$ and $10^{14}$ pfu, and preferably $10^6$ to $10^{11}$ pfu. The term pfu (plaque forming unit) corresponds to the infectivity of a virus solution, and is determined by infecting an appropriate cell culture and measuring, generally after 15 days, the number of plaques of infected cells. The technique for determining the pfu titre of a viral solution are well documented in the literature.

In a preferred embodiment, the composition comprises an adenovirus comprising the anti-angiogenic factor gene, e.g., ATF gene (AdATF) or angiostatin (AdK3), in a concentration of about $1 \times 10^9$ pfu/100 $\mu$l.

The compositions according to the invention are particularly useful for administration to tumors.

Tumors. The present invention is directed the treatment of tumors, particularly solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In another embodiment, dysproliferative changes (such as metaplasias and dysplasias) are treated or prevented in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2 d Ed., W. B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, *Medicine*, 2 d Ed., J. B. Lippincott Co., Philadelphia.

The present invention is also directed to treatment of non-malignant tumors and other disorders involving inappropriate cell or tissue growth augmented by angiogenesis by administering a therapeutically effective amount of a vector of the invention to the tissue undergoing inappropriate growth. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; and benign prostatic hypertrophy, a condition associated with inflammation and possibly vascular proliferation. Treatment of other hyperproliferative disorders is also contemplated.

Methods of administration. According to the invention, the preferred route of administration to a tumor is by direct injection into the tumor. The tumor can be imaged using any of the techniques available in the art, such as magnetic resonance imaging or computer-assisted tomography, and the therapeutic composition administered by stereotactic injection, for example.

Alternatively, if a tumor target is characterized by a particular antigen, a vector of the invention can be targeted to the antigen as described above, and administered systemically or subsystemically, as appropriate, e.g., intravenously, intraarterioally, intraperitoneally, intraventricularly, etc.

Combination Therapies. Although the methods of the invention are effective in inhibiting tumor growth and metastasis, the vectors and methods of the present invention are advantageously used with other treatment modalities, including without limitation surgery, radiation, chemotherapy, and other gene therapies.

For example, the vectors of the invention can be administered in combination with nitric oxide inhibitors, which have vasoconstrictive activity and reduce blood flow to the tumor.

In another embodiment, a vector of the invention can be administered with a chemotherapeutic such as, though not limited to, taxol, taxotere and other taxoids [e.g., as disclosed in U.S. Pat. Nos. 4,857,653; 4,814,470; 4,924,011, 5,290,957; 5,292,921; 5,438,072; 5,587,493; European Patent No. 0 253 738; and International Patent Publication Nos. WO91/17976, WO93/00928, WO93/00929, and WO9601815], or other chemotherapeutics, such as cis-platin (and other platin intercalating compounds), etoposide and etoposide phosphate, bleomycin, mitomycin C, CCNU, doxorubicin, daunorubicin, idarubicin, ifosfamide, and the like.

In still another embodiment, a vector of the invention can be administered in conjunction with another gene therapy for tumors, such as but by no means limited to p53 or analogues thereof such as CTS-1 [WO97/04092], thymidine kinase (TK), anti-RAS single chain antibodies, interferon-α or interferon-γ, etc., as described above. Any vector for gene therapy can be used in conjunction with the present invention, such as a viral vector or naked DNA. In a preferred embodiment, a single vector (virus or DNA) is used to deliver genes coding for both an anti-angiogenesis factor and another tumor therapy gene.

In another aspect, the present invention provides for regulated expression of the anti-angiogenic factor gene in concert with expression of proteins useful in the context of treatment for proliferative disorders, such as tumors and cancers, when the heterologous gene encodes a targeting marker or immunomodulatory cytokine that enhances targeting of the tumor cell by host immune system mechanisms. Examples of such heterologous genes for immunomodulatory (or immuno-effector) molecules include, but are not limited to, interferon-α, interferon-γ, interferon-β, interferon-ω, interferon-τ, tumor necrosis factor-α, tumor necrosis factor-β, interleukin-2, interleukin-7, interleukin-12, interleukin-15, B7-1 T cell costimulatory molecule, B7-2 T cell costimulatory molecule, immune cell adhesion molecule (ICAM)-1 T cell costimulatory molecule, granulocyte colony stimulatory factor, granulocyte-macrophage colony stimulatory factor, and combinations thereof.

The present invention will be better understood be reference to the following Examples, which are provided by way of exemplification and not by way of limitation.

EXAMPLE 1

Gene Therapy With ATF Inhibits Tumor Growth and Metastasis

Example 1 demonstrates that expression of the uPA/uPAR antagonist ATF (amino terminal fragment of urokinase) inhibits tumor growth and metastasis. A defective adenovirus expressing murine ATF from the CMV promoter (AdmATF) was constructed. A single intratumoral injection of AdmATF inhibited growth of pre-established tumors in two different murine models, and delayed tumor dissemination. These effects were correlated with a remarkable inhibition of neovascularization within, and at the immediate vicinity of, the injection site. The magnitude of this effect was particularly remarkable in the ability of murine ATF to inhibit angiogenesis of a human-derived tumor.

Methods

Figure 1:
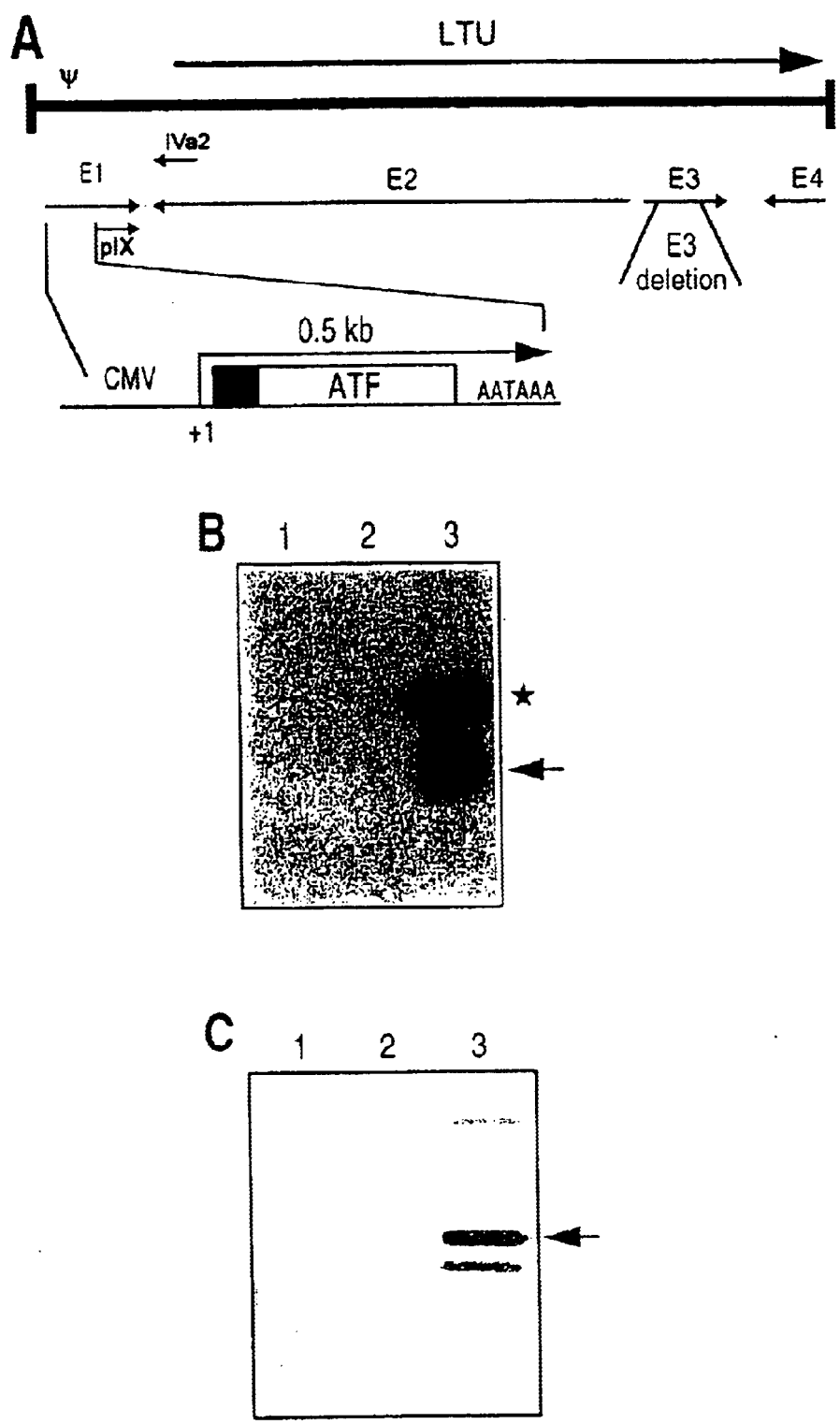
FIG. 1. Molecular characterization of virus AdmATF. Panel A: Structure of AdmATF and AdCO1. The Ad5 chromosome is 36 kb long and bordered by inverted terminal repeats. Y refers to the encapsidation signal. Both viruses are defective for growth because they lack the Ad5 E1 genes. They also carry a 1.9 kb XbaI deletion within region E3. A schematic representation of the mATF expression cassette of virus AdmATF is indicated under the Ad5 chromosome (not drawn to scale). For a review on adenoviral vectors see (38). Panel B: analysis of mATF expression. MDA-MB-231 cells were infected for 24 hr by AdCO1 (lane 2) or AdmATF (lane 3), or mock-infected (lane 1), and total poly(A+) RNAs were submitted to northern blot analysis. The ATF-encoding RNA (0.5 kb) is indicated (arrow). A 1.7 kb molecule is also detected (asterisk), a size in agreement with the utilization of the polyadenylation signal from the adenovirus pIX gene. Panel C: analysis of ATF secretion by 293-infected cells.

Recombinant adenoviruses. AdmATF is an E1-defective recombinant adenovirus that expresses the murine ATF gene from the CMV promoter. Plasmid pDB1519 16 was used as starting material to introduce a stop codon after residue 135 of mature uPA. Briefly, the uPA-encoding sequences (including its signal peptide) were isolated, restricted by NsiI, and residues 128 to 135 followed by a stop codon were reintroduced as a synthetic fragment. The ATF open reading frame was then inserted between the CMV promoter and the SV40 late polyadenylation signal sequence, generating plasmid pEM8-mATF. This plasmid also carries the first 6.3 kb of the Ad5 genome except that the ATF expression cassette has been inserted between position 382 and 3446, in place of the E1 genes (FIG. 1A). AdmATF was constructed in 293 cells by homologous recombination between pEM8-mATF and ClaI-restricted AdRSVbGal DNA 25. Individual viral plaques were isolated onto 293-derived cell monolayers grown in soft agar, amplified onto fresh 293 cells and viral DNA was extracted 26. EcoRI, EcoRV and AvrII+NdeI restriction analyses confirmed the identity and clonality of the recombinant adenovirus. AdCO1 is a defective control adenovirus that is identical to AdmATF except that it does not carry any transgene expression cassette in place of E1. Both viruses were propagated in 293, a human embryonic kidney cell line that constitutively expresses the E1 genes of Ad5 27. Viral stocks were prepared and titrated as described 25. Unless otherwise stated, MDA-MB-231 cells and Lewis lung carcinoma (LLC) cells were infected at a multiplicity of infection (MOI) of 300 PFU/cell. These infection conditions were previously shown to translate respectively into 80 and 65% of b-galactosidase-expressing cells when virus AdRSVbGal 25 was used.

Northern blot analysis. Subconfluent MDA-MB-231 cell cultures were infected with AdmATF or AdCO1, and total RNA was extracted 24 hr post-infection (p.i.) by the RNA-ZOL procedure (Biogentex, Inc), and polyadenylated RNAs were purified. The samples were run in a 1% formaldehyde agarose gel, and transferred onto Hybond N membranes (Amersham). The membranes were prehybridized with denatured sonicated salmon sperm DNA (100 µg/ml) for 1 hr at 42° C. in 10 ml of 50% deionized formamide, 0.2% SDS, 5× Denhardt's solution, and incubated overnight with a random-primed ($^{32}$P)-labeled 1.2 kb XbaI-HindIII fragment from murine uPA cDNA (16). The membranes were washed twice in 2×SSC/0.1% SDS for 1 hr at 50° C., once in 0.1×SSC for 30 min, and expose Kodak-XAR-5 films for 1 hr at room temperature.

Western blot analysis. Supernatants from virally-infected cells were collected 24 hr p.i., run in a 12.5% SDS-polyacrylamide gel (400 µg of protein per lane), prior to transfer onto a nitrocellulose membrane (Schleicher & Schuell). After incubation for 1 hr in blocking buffer, the membranes were incubated for 1 hr with a polyclonal serum raised against murine uPA (Pr. R Lijnen, Leuven, Belgium), then for an additional hour with a horse-radish peroxidase-conjugated goat anti-rabbit serum (Dako). The membranes were washed three times in PBS-Tween buffer, and incubated with 3-Amino-9-ethyl-Carbazole (AEC) for 5 min.

Inhibition of cell-associated proteolysis. Native uPA was first dissociated from its cell surface receptor by submitting LLC cell monolayers to a 3 min acidification in glycine-HCl (pH 3), followed by incubation in 0.5 M HEPES buffer. The cells were then incubated for 20 min at 37° C. with the supernatant of AdCO1- and AdmATF-infected 293 cells. After 3 washes in PBS/0.1% BSA, the cells were incubated at 37° C. for 20 min with 1 nM of murine uPA (Pr. R. Lijnen, Leuven, Belgium). Unbound uPA was then removed by washing in PBS, and cell-associated uPA was quantified by adding 0.4 µM of human plasminogen and plasmin substrate S-2251 (Kabi Vitrum, Sweden).

In vitro invasion assay. Twenty four hr p.i., LLC cells were detached with 1 mM EDTA, washed in PBS, and resuspended in FCS-free MDEM medium supplemented with 0.1% BSA. Invasion assays were carried out in a transwell unit as described (19). Briefly, polycarbonate filters of 1.2 µm pore size (Transwell, Costar) were coated with 160 µg Matrigel (Becton Dickinson) and dried. The lower chambers of the Transwell units were filled with human fibroblast-conditioned medium containing 10 ng/ml EGF, and the upper chambers were seeded with 3×10$^5$ infected cells. After 24 hr incubation at 37° C., the number of cells that had reached the lower chamber was determined under a light microscope following staining with Giesma.

Syngeneic tumor model. Lewis lung carcinomas were serially passaged onto C57BL/6 syngeneic mice. Briefly, C57BL/6 implanted subcutaneously with a LLC tumor were sacrificed when the tumor had reached a volume of 600–1200 mm$^3$. Tumor cells were resuspended in a 0.9% saline solution following filtration through a cotton sieve, and 2×10$^6$ cells (0.5 ml) were subcutaneously implanted to the dorsa of 6–7 weeks-old C57BL/6 female mice. After 5 days, the tumors had reached a size of approximately 20 mm$^3$, and they were injected with 0.2 ml of PBS (n=8), or 10$^9$ PFU (0.2 ml) of AdCO1 (n=10) or AdmATF (n=10). The size of the primary tumor was measured at day 5, 10 and 15 p.i. At day 16 p.i., the number of lung metastases was assessed 3 hr after an intraperitoneal injection of 65 mg BrdU. Lung tissues were removed, fixed overnight in acetic formaldehyde acid (AFA), and paraffin sections were incubated 15 min in 4 N HCl, neutralized and saturated by washing twice for 15 min in PBS/0.5% BSA/0.1% Tween 20 prior to incubation with peroxidase-labeled mouse anti-BrdU monoclonal antibody (Boehringer) for 45 mm at 37° C., and AEC. BrdU-positive foci were quantified under a light microscope at a magnification of 25.

Athymic murine model. Cultured MDA-MB-231 cells (ATCC HTB 26) were harvested, washed, resuspended in PBS at 1.5×10$^7$ cells/ml, and 3×10$^6$ cells were subcutaneously injected in the dorsa of 6–7 weeks old nude mice. When the tumors had reached a volume of 15–20 mm$^3$ (i.e., after 11 days), the animals received an intratumoral injection of 10$^9$ PFU of AdmATF (n=5) or AdCO1 (n=5), or PBS (n=5), and the size of the tumors was monitored until day 52 p.i., after which the animals were sacrificed and the extent of intratumoral vascularization was assessed as described (28). Briefly, tumor tissues were fixed overnight in AFA, transferred to 100% ethanol, embedded in paraffin and 5 μm thick sections were prepared. After toluene treatment and rehydration, the sections were permeabilized with 2 μg/ml proteinase K at 37° C. for 15 min. Endogenous peroxidase activity was quenched by 0.3% $H_2O_2$ for 15 min. The sections were washed with PBS, incubated 15 min in 7.5% BSA, and incubated 30 min with a rabbit polyclonal serum raised against human vWF (Dako). After two washes in PBS, the sections were incubated with biotinylated goat anti-rabbit IgG antibodies for 30 min, washed, and incubated with streptavidin-peroxidase for 15 min prior to addition of AEC. Neovascular hotspots were first identified at low magnification and vWF-positive microvessels were quantified. Meyer's hematoxylin was used for counterstaining as described (28).

To evaluate AdmATF infection on tumor establishment, confluent MDA-MB-231 cells were first infected with AdmATF or AdCO1 at an MOI of 50 PFU/cell. The cells were washed 24 hr p.i., resuspended in 120 μl PBS, mixed with 80 μl ice-cold Matrigel, and $1.3 \times 10^6$ cells were subcutaneously implanted into the dorsa of nude mice. Tumor establishment and growth were followed until day 51 after implantation.

Results

Molecular and functional characterization of AdmATF. AdmATF is a defective recombinant adenovirus that expresses murine ATF from the CMV promoter whereas AdCO1 is an "empty" control adenovirus (FIG. 1A). In vitro studies were first carried out to characterize AdmATF with regards to its ability to express a functional uPA antagonist following infection. ATF gene expression was demonstrated by northern analysis of poly(A+) RNAs extracted from MDA-MB-231 cells infected for 24 hr with AdmATF, but not AdCO1 (FIG. 1B). Secretion of ATF by AdmATF-infected cells was demonstrated for 293, LLC and MDA-MB-231 cells by Western blot analysis. For example, an ATF-specific polypeptide with a molecular weight corresponding to that of the mature peptide (15.3 kDa) is uniquely detected in the medium from 293 cells infected for 24 hr p.i. with AdmATF (FIG. 1C).

ATF is a potent antagonist of uPA binding to its cell surface receptor (uPAR), and disruption of this complex is known to greatly inhibit the conversion of inactive plasminogen into plasmin. LLC cell-associated plasmin conversion was thus measured to assess the functionality of ATF secreted by AdmATF-infected cells. As a prerequisite, we checked that LLC cells displayed significant levels of cell-associated uPA activity (data not shown), implying that they secrete uPA and express uPAR. Plasmin conversion/activity was significantly reduced when endogenous uPA had been previously removed from the cell surface by a mild acid treatment prior to incubation with the supernatant of AdmATF-infected 293 cells and addition of 1 nM murine uPA (FIG. 2A).

The uPA/uPAR complex is also crucial to cell motility. An in vitro cell invasion assay was used to confirm the functionality of AdmATF. LLCs cells were infected with AdmATF or AdCO1, and the number of cells that had migrated through a matrix-coated membrane was determined after 24 hr (FIG. 2B). Quantification of the data demonstrated that AdmATF infection inhibited LLC invasiveness by 65% (n=5) as compared to AdCO1 control infections.

Intratumoral injection of AdmATF inhibits tumor growth and dissemination. We first used the Lewis lung carcinoma-C57B1/6 syngeneic model to evaluate the antitumoral effects associated with a single intratumoral administration of AdmATF. Five days after subcutaneous implantation, the tumors were injected with $10^9$ PFU of AdmATF, $10^9$ PFU of AdCO1, or PBS, and tumor growth was monitored until day 15 p.i. As shown in FIG. 3, an overall inhibition was specifically observed in the AdmATF-treated group. The animals were then sacrificed at day 16 p.i., and lung metastases were numbered by counting the number of BrdU-positive foci. Whereas metastases were apparent in all animals injected with PBS (n=8), 7 out of 9, and only 3 out of 9 scored positive within the AdCO1- and AdmATF-treated groups, respectively. The average number of BrdU-positive foci per lung sections was also reduced in the AdmATF-treated group (2.7) as compared to that in the AdCO1-treated (6.3) and PBS-treated (6.6) groups. A single intratumoral administration of AdmATF therefore significantly inhibited tumor growth and lung dissemination in this highly aggressive model. In a separate experiment, tumor-bearing animals were infected with AdCO1 or AdmATF, and the tumors extracted at day 10 and 20 p.i. for macroscopic inspection. While AdCO1-injected LLC tumors displayed an intense vascularization at both time points, tumors from the AdmATF-treated group displayed only marginal vascularization (FIG. 4).

The antitumoral effects of AdmATF are exerted at the level of angiogenesis. To specifically evaluate the sole inhibition of angiogenesis for tumor growth, we studied adenovirus-mediated delivery of the murine uPA/uPAR antagonist in the human-derived MDA-MB-231 breast carcinoma model implanted into athymic mice. A direct action of murine ATF on the tumor cells should be minimal in this model as murine uPA binds human uPAR 200-fold less efficiently than murine uPAR. Eleven days after subcutaneous tumor cell inoculation, the animals received a single intratumoral injection of $10^9$ PFU of AdmATF, 109 PFU of AdCO1, or PBS, and tumor growth was monitored until day 52 p.i. While no significant effect were apparent until day 32 p.i., an arrest of tumor growth then became evident in the AdmATF-infected, but not the AdCO1-infected group (FIG. 5). Mice were sacrificed at day 52 p.i., and intratumoral angiogenesis was assessed by visualization of von Willebrand Factor (vWF)-immunoreactive vessels (FIG. 6A). An average of 4 to 6 vessels were detected within the sections from the AdmATF-treated tumors as compared to 18 to 20 in the sections from the AdCO1-injected tumors. Tumors injected with AdmATF also displayed little peripheral neovascularization as compared to their AdCO1-treated counterparts (FIG. 6B). When MDA-MB-231 cells were first infected in vitro before subcutaneous inoculation in the presence of Matrigel, tumors became apparent in the AdCO1-treated group as early as 7 days post-implantation. A tumor of limited size was apparent in only one animal from the AdmATF-treated group (n=5), in sharp contrast to the larger tumors present in 4 out of 5 animals from the AdCO1-infected group. Again, the tumor that had developed following inoculation of AdmATF-infected tumor cells was less vascularized than those that developed following inoculation of AdCO1-infected cells (data not shown).

Discussion

We have studied the antitumoral effects associated with the local delivery of the amino-terminal, non-catalytic, fragment of urokinase (ATF), a potent antagonist of urokinase binding to its receptor (uPAR) at the surface of both tumor (19, 20) and endothelial cells (22, 23). In vivo delivery of ATF was achieved by intratumoral administration of a defective adenovirus that expresses a secretable ATF molecule of murine origin from the CMV promoter (AdmATF). To exclude non-specific cytotoxic effects consecutive to virus infection (29), an "empty" otherwise isogenic adenovirus (AdCO1) was used as a control virus throughout the study. This is an important control also because recombinant adenoviruses can use the aVb3 integrin for infection (30), a cell surface receptor somehow involved in tumor growth and angiogenesis (31).

A single intratumoral injection of AdmATF is efficient in reducing tumor growth (FIG. 3) and delaying dissemination to the lungs in the aggressive LLC-C57BL/6 syngeneic murine model. Murine ATF apparently partly exerted these effects by inhibiting the invasiveness of the tumor cell themselves (FIG. 2B), a result consistent with the inhibition of cell-associated proteolysis following AdmATF infection (FIG. 2A). ATF-based antagonists are also potent inhibitors of endothelial cells motility (22, 23), suggesting that inhibition of tumor angiogenesis may have also contributed to the effects observed in this model. Indeed, LLC tumors injected with AdmATF displayed very little vascularization as compared to AdCO1-infected control tumors (FIG. 4). That specific AdmATF-mediated tumor growth inhibition became evident at late time p.i. but not so much at early time likely results from lesser requirements of smaller tumors (typically below 300 mm3, see FIG. 3 and FIG. 5) for neovascularization to provide the growth nutrients (for a review see 24).

Inhibition of LLC cells dissemination to the lungs was only transient as the survival rate from the AdmATF-treated group was only slightly extended (less than 30 days after tumor implantation) as compared to that from the AdCO1-treated group (less than 25 days). The effects of AdmATF injection on tumor cells dissemination may be explained either because the tumor cells were frozen following AdmATF infection, and/or because few vessels were available for entry into the vasculature. That dissemination did eventually occur suggests that some tumor cells may have had already reached the vasculature at the time of AdmATF injection. Alternatively, infection with E1-deleted adenoviruses is also typically associated with a rapid clearance of the infected cells in C57BL/6 mice immunotolerant for the transgene product (29), and ATF is a small molecule that exhibits a very short half-life in vivo.

Preclinical data indicate that the uPA/uPAR complex is critically involved in controlling cell migration, including that of endothelial cells. For example, an ATF-IgG fusion protein with an extended in vivo half-life has been shown to inhibit angiogenesis and tumor growth in a bFGF-enriched Matrigel murine model (23). The present study provides evidence that the antitumoral effects of uPA/uPAR antagonists are essentially exerted by controlling intratumoral and peripheral angiogenesis: whereas the antitumoral effects of AdmATF-mediated gene delivery may have been multifactorial as both tumor and endothelial cells are potential targets in the syngeneic tumor model, this is not the case in the MDA-MB-231/athymic murine model because mATF is a poor antagonist of uPA/uPAR complex formation at the surface of human cells, including MDA-MB-231 (32). A remarkable feature that emerged in the MDA-MB-231 model was the efficacy of AdmATF in preventing tumor growth (FIG. 5) and neovascularization within and at the vicinity of the tumor (FIG. 6). In contrast, tumors infected with the control adenovirus were still capable of "attracting" adjacent vessels. The antitumoral properties of AdmATF are further illustrated in this model by the reduced efficacy of tumor establishment following infection.

Malignant tumors are life-threatening because they invade and abrogate the function of vital organs at distant sites, emphasizing the importance of targeting angiogenesis to fight cancer (33; see also 34). First, growth of primary tumors relies on neovascularization to provide the required nutrients. Second, metastases have also been reported to undergo apoptosis in the absence of neovascularization (35). Furthermore, growing capillaries within the tumor are "leaky": they exhibit a fragmented basal membrane (36), a prerequisite for efficient penetration of the tumor cells into the vasculature (37). The overall results of this study demonstrate that significant antitumoral effects can be achieved following a single intratumoral administration of a recombinant adenovirus expressing a potent antagonist of uPA/uPAR function at the cell surface, and that these effects mostly result from an inhibition of angiogenesis. Applying this approach to invasive solid tumors is certainly attractive for cancer gene therapy because of the pleiotropic clinical effects expected following inhibition of tumor angiogenesis.

EXAMPLE 2

Gene Therapy With Angiostatin Inhibits Tumors In Vivo

Example 2 demonstrates that expression of the amino terminal fragment of human plasminogen (angiostatin K3) inhibits tumor growth in vivo by blocking endothelial cell proliferation associated with a mitosis arrest. The antitumoral effects that follow the local delivery of the N-terminal fragment of human plasminogen (angiostatin K3) have been studied in two xenograft murine models. Angiostatin delivery was achieved by a defective adenovirus expressing a secretable angiostatin K3 molecule from the CMV promoter (AdK3). In in vitro studies, AdK3 selectively inhibited endothelial cell proliferation, and disrupted the G2/M transition induced by M-phase-promoting factors. AdK3-infected endothelial cells showed a marked mitosis arrest that correlated with the downregulation of the M-phase phosphoproteins. A single intratumoral injection of AdK3 into pre-established rat C6 glioma or human MDA-MB-231 breast carcinoma grown in athymic mice was followed by a significant arrest of tumor growth, that was associated with a suppression of neovascularization within and at vicinity of the tumors. AdK3 therapy also induced a 10-fold increase in apoptotic tumor cells as compared to control adenovirus. The data support the concept that targeted anti-angiogenesis, using adenovirus-mediated gene transfer, represents a promising strategy for delivering anti-angiogeneic factors as bolus injections of anti-angiogenic proteins still present unsolved pharmacological problems.

Methods

Construction of AdK3. AdK3 is an E1-defective recombinant adenovirus that expresses the N-terminal fragment of human plasminogen (up to residue 333) from the CMV promoter. Human Plg cDNA was obtained from plasmid PG5NM119. A fragment encoding the 18 aa signal peptide of Plg, followed by the first 326 residues of mature Plg was first subcloned between the BamHI and ScaI sites of plasmid pXL2675. A synthetic oligodeoxynucleotide encoding residues 327 to 333 followed by a stop codon was then added, prior to inclusion between the CMV promoter and the SV40 late polyadenylation signal. This expression cassette was then inserted between the EcoRV and BamHII sites of plasmid pCO5 to generate plasmid pCO5-K3. AdK3 was constructed in 293 cells by homologous recombination between pCO5-K3 and ClaI-restricted AdRSVβgal DNA

[25]. Individual plaques were isolated onto 293-derived cell monolayers, amplified onto fresh 293 cells and viral stocks were prepared as described [25]. AdCO1 is a control virus that is identical to AdK3 except that it does not carry any expression cassette.

Cell lines maintenance and infection. C6 glioma cells (ATCC CCL-107) and MDA-MB 231 cells (ATCC HTB 26) were cultured in DMEM with 10% of fetal calf serum (FCS). Viral infection was performed with 5% FCS. Human Microcapillary Endothelial Cells (HMEC-1) [49] were cultured in MCDB 131 supplemented with 20% of FCS, 1 mM L-glutamine, 1 µg/ml of hydrocortisone, 10 ng/ml of epithelium growth factor and infection was performed in the same medium but with 10% of FCS and 3 ng/ml of recombinant human b-FGF (R&D system). The multiplicity of infection (MOI) was chosen as to obtain between 80% to 100% infected cells as judged by X-GAL staining following infection with virus AdRSVβGal.

Western blot analysis. Subconfluent cells were infected with AdK3 or AdCO1 at an MOI of 300 plaque-forming units (PFU)/cell. Cell culture supernatants were collected 48 to 96 hr post-infection (p.i.). For in vivo immunological analysis of the K3 angiostatin molecule, the tumors were collected at day 10 p.i., frozen in liquid nitrogen, powdered, extracted with lysis buffer (10 mM NEM, 1% triton X100, 1 mM PMSF, 0.1 M $NH_4OH$) and centrifuged at 12000 rpm at 4° C. The samples with 300 µg o protein were run in a 10% SDS-polyacrylamide gel, prior to being transferred onto a nitrocellulose membrane (Schleicher & Schuell). 100 ng human Plg (Stago) was run as a control. After 2 hr incubation in blocking buffer (TBS-5% milk-0.05% Tween 20), the membranes were incubated for 1 hr with anti-human Plg MAb A1D12 [50], 1 hr with a horseradish peroxidase-conjugated goat anti-mouse serum (Biosys). After washing, the membranes were detected with ECL bioluminescence kit (Amersham, UK). To detect the MPM-2 phosphoepitope, the extracts were prepared from the HMEC-1 cell 96 hr p.i. and probed with the specific mitotic MPM-2 MAb (DAKO).

Proliferation assay. Tumor or HMEC-1 cells were infected with AdK3 or AdCO1 at the indicated MOI for 12 hr. The cells were collected with 1 mM EDTA, washed twice with PBS and resuspended. They were seeded into 96-well culture plates (5000 cells/well) and cultured for 72 hr. In addition, HMEC-1 cells were cultured in MCDB131 medium containing 40, 20 or 10% supernatant of AdK3 or AdCO1-transduced C6 glioma cells. Supernatants from virally-infected C6 cells were collected 96 hr p.i., heated 30 min at 56° C. in order to inactivate the virus, concentrated 10 times and dialyzed against PBS. Cells were quantified with a cell proliferation assay kit using a MTS tetrazolium compound (Promega).

Formation of capillary tube in a fibrin matrix model. This model was devised according to the method of Pepper et al [51] using Calf Pulmonary Artery Endothelial cells (CPAE) (ATCC CCL 209) infected for 12 hr with AdK3 or AdCO1 at an MOI of 600.

Whole blood lysis assay. Whole blood clot lysis was performed by mixing 80 U/ml of tissue-plasminogen activator, 250 µl of culture supernatant obtained 4 days p.i. with AdK3 or AdCO1, and 500 µl of citrate-anti-coagulated whole blood collected from healthy donors. Coagulation was triggered by adding 1 U/ml of thrombin and of 12 mM Ca++. The extent of clot lysis was determined by lysis time and by following the kinetics of soluble D-Dimers as described [52].

Immunoflow cytometry. HMEC-1 were infected for 96 hr with AdK3 or AdCO1 at an MOI of 300 PFU/cell. The cells were collected, permeabilized with triton X100, incubated with iodide propidium (20 µg/ml) and ribonuclease A (100 µg/ml) for 30 min at room temperature to label DNA, prior to incubation with mitotic MPM-2 antibody as described [53]. FITC-conjugated anti-mouse IgG antibodies were used to detect MPM-2 phosphoepitope. The experiment was performed in a Coulter EPICS Profile II flow cytometer and the data were analysed by Multicycle software (Phoenix Flow Systems, San Diego, Calif.).

Athymic murine models. Cultured C6 glioma cells and MDA-MB-231 cells were harvested, washed, resuspended in PBS at $1.5 \times 10^7$ and $0.25 \times 10^7$ cells/ml respectively and a volume of 200 µl subcutaneously injected into the dorsa of 6–7 weeks old nude mice. When the tumors had reached a volume of 20 $mm^3$, the animals received an intratumoral injection of $10^9$ PFU of either AdK3 (n=6), or AdCO1 (n=6), or PBS (n=6). Tumor size was monitored until day 10 p.i. for the C6 glioma model, and day 42 p.i. for the MDA-MB-231 model.

To assess the effect of AdK3 infection on tumor establishment and progression, MDA-MB-231 and C6 cells were infected for 24 hr at an MOI of 50 and 100 PFU/cell, respectively, prior to subcutaneous inoculation into the dorsa of nude mice (n=6). Infected MDA-MB-231 cells are less tumorigenic than infected C6 cells so 80 µl ice-cold Matrigel (Becton Dickinson) had to be added to 120 µl of PBS prior to subcutaneous implantation ($10^6$ MDA-MB-231 or $0.25 \times 10^6$ C6 cells). Tumor establishment and growth were followed until day 25 (MDA-MB-213) or day 22 (C6) p.i. A Student's t-test was used for statistical analysis.

Immunohistochemistry. Tumor tissues were fixed in alcohol formalin acetic acid, embedded in paraffin and 5 µm sections were prepared. After toluene treatment and rehydration, the sections were pretreated three times for 5 min in a microwave oven in 10 mM citrate buffer (pH 6.0), quenched by 3% $H_2O_2$ for 5 min to remove endogenous peroxidase activity, washed in PBS, then incubated with a rabbit polyclonal serum raised against human von Willebrand factor (vWF; Dako, dilution 1:200) for 60 min. After 3 washes, the sections were incubated with biotinylated goat anti-rabbit IgG antibodies for 30 min., washed, and incubated with streptavidin-peroxidase for 30 min. prior to addition of 3-Amino-9-ethyl-carbazole. Meyer's hematoxylin was used for counterstaining. Apoptotic cells within the section were detected by a kit using a terminal deoxynucleotidyl transferase-mediated dUTP-biotin nick end labeling method (TUNEL) (Boehringer Mannheim). For proliferating cell nuclear antigen (PCNA) staining procedure included a biotinylated mouse anti-PCNA antibody (Pharmingen, dilution 1:100) followed by streptavidin peroxidase and substrate revelation.

Results

Molecular characterization of AdK3. Recombinant AdK3 carries a CMV-driven N-terminal fragment of human Plg that includes the first three kringle domains of the angiostatin molecule [47], whereas AdCO1 is an "isogenic" control adenovirus that does not encode any expression cassette (FIG. 7A). Secretion of the K3 molecule in the culture media 2–3 days after infection with AdK3 was demonstrated for HMEC-1, C6 and MDA-MB-231 cells by Mab A1D12 immunoblotting, whereas no signal was detected following infection with AdCO1 (FIG. 7B). The secreted immunoreactive peptide appeared as a doublet with a molecular weight of 36 and 38 kDa, most likely reflecting a different extent of N-glycosylation at $Asn^{289}$ as described for Plg [54, 55].

Functional characterization of AdK3. Transduction of HMEC-1 by AdK3 resulted in an inhibition of bFGF-stimulated proliferation in a dose-dependent manner at day 3 p.i.: 30% at an MOI of 50, 74% at an MOI of 150, and 97% at an MOI of 300, in sharp contrast to the cells infected with AdCO1 (P<0.005). AdK3 did not affect MDA-MB-231 and C6 cell proliferation (FIG. 8A). To assess the paracrine potential of the K3 molecule to exert these effects, virus-free culture media from virally-infected C6 glioma cells were added to HMEC-1 cells. As illustrated in FIG. 8A, we did observe a dose-dependent inhibition of HMEC-1 cell proliferation by C6 cell-secreted angiostatin (p<0.001). The addition of AdK3 also significantly inhibited the capillary formation of CPAE cells in fibrin gel with a 55% mean reduction (not shown). Moreover, whole blood clot lysis induced by tPA was not inhibited by the addition of cell culture supernatants from AdK3-infected C6 cells, and the generation of D-Dimers was basically unchanged during the first three hours (1200 ng/ml versus 1150 ng/ml).

AdK3 inhibits mitosis of endothelial cells. To determine if angiostatin is able to block the mitosis of HMEC-1, a flow immunocytometry analysis was performed with the cells labeled with MAb MPM-2 that binds to the phosphorylated proteins specifically present during the M-phase, together with concurrent DNA staining. The results showed that mitosis of AdK3-infected HMEC-1 cells was decreased by 82% relative to AdCO1 infection: only 5% of HMEC-1 cells within the G2/M pic scored positive for MPM-2 following infection with AdK3 as compared to 27% following AdCO1 control infection (FIG. 8C). Western blot analysis was performed from HMEC-1 extracts in order to detect MPM-2 positive proteins as at least 16 mitotic phosphoproteins were usually revealed by MPM-2 with an apparent molecular weight ranging from 40 to more than 200 kDa. As compared to control extracts from non-infected or AdCO1-infected HMEC-1 cells, extracts from AdK3-infected cells exhibited a markedly reduced level of MPM2-reactive phosphoproteins (FIG. 8B).

AdK3 inhibits tumor growth. To induce local secretion of angiostatin, a single dose of $10^9$ PFU of AdK3 was injected into 20 $mm^3$ pre-established human MDA-MB-231 breast carcinoma and rat C6 glioma tumors grown in athymic mice, and tumor growth was monitored. As shown in FIG. 9A, C6 tumors from the AdK3-injected group were significantly smaller than those from the AdCO1 or the PBS control groups: at day 10 p.i., AdK3-injected tumors had reached a mean volume of 278±14 $mm^3$ versus 1403±142 $mm^3$ or 1583±259 $mm^3$ for AdCO1- and PBS-injected tumors, respectively (p<0.05). This 80% inhibition correlated with the detection of angiostatin-immunoreactive material (FIG. 7C). As shown in FIG. 9B, tumor growth was similarly inhibited (85%) in the MDA-MB-231 tumor model at day 42 p.i.: 80±4 $mm^3$ for AdK3-treated tumors versus 563±137 $mm^3$ for AdCO1- and 530±69 $mm^3$ for PBS-injected tumors respectively (p<0.05).

AdK3 inhibits angiogenesis and induces tumor cell apoptosis in vivo. C6 tumors infected with AdCO1 appeared much more vascularized than their AdK3-infected counterparts (FIG. 10, panels A–B). Intratumoral angiogenesis was thus assessed by vWF-immunostaining of tumor sections as described [28]. vWF-positive hotspots were first localized at low magnification, and vWF-positive vessels were then counted at 200×magnification (FIG. 10, panels E–F). The results indicated a marked reduction of intratumoral vascularization within AdK3-injected tumors (5±2 vWF-positive vessels per field) as compared to the AdCO1-injected control (14±4; n=5, p<0.005). Tumors in the PBS-injected group exhibited an identical number of vessels (14±3) indicating that the infection conditions used did not interfere with tumor angiogenesis. At the macroscopic level, C6 tumors injected with AdK3 displayed little peripheral neovascularization as compared to their AdCO1-treated counterparts (FIG. 10, panels C–D). Similar results were obtained within MDA-MB-231 tumor sections (4.8±1.2 vWF-immunoreactive vessels/field for AdK3 versus 15.6±3 for AdCO1, p=0.02).

Tumor cell apoptosis was then quantified in situ with the C6 tumor samples by the TUNEL method (see Methods). The results indicated a marked increase of apoptotic cells in the AdK3-injected C6 tumors 10 days p.i. (20±9 versus 1–2 apoptotic cells per field for control tumors, p<0.001) (FIG. 10, panels G–H). In contrast, the tumor cell proliferation rate was not different among the three animal groups as assessed by PCNA immunostaining (not shown). Ad-angiostatin therapy induced a 10 fold increase in apoptotic tumor cells without affecting the proliferation of these cells, similar to the reported results obtained by daily injections of purified angiostatin.

AdK3 inhibits tumorigenesis. To determine whether inhibition of tumor angiogenesis attenuated tumorigenesis, MDA-MB-231 and C6 cells were first infected for 24 hr prior to injection into the dorsa of nude mice. After 5 days, all the mice from the AdCO1-infected group developed hypervascularized C6 tumors with an average size of 27.4±3.41 $mm^3$, whereas 20% of animals from the AdK3-infected group remained tumor free after 12 days (FIG. 11). The remaining animals exhibited very small tumors (average size of 0.42±0.05 $mm^3$) that were hardly vascularized. After 22 days, the tumors that were observed within the AdK3 group were at least 5-fold smaller than those from the AdCO1 group (n=5, p<0.005; FIG. 11). Similar observations were made with the MDA-MB-231 tumor model (not shown).

Discussion

Angiostatin has been shown to be a physiopathological inhibitor of angiogenesis secreted by primary tumors, driving the metastasis into a dormant state. It was therefore tempting to assess the therapeutic potential of angiostatin on primary tumors. However, systemic and intraperitoneal bolus injections of human angiostatin have underlined difficult pharmacological problems because angiostatin is rapidly cleared from the circulation [46]. A prolonged exposure of purified angiostatin at high doses was indeed required to maintain cytostatic intratumoral concentrations of angiostatin [46]. It was not clear that direct transduction of the tumor and the surrounding tissue with a recombinant virus encoding an angiostatin cDNA would represent a more efficient method of achieving constant intratumoral concentrations of angiostatin. Adenoviruses are appropriate vectors in such a strategy as they can efficiently express their transgene at therapeutic levels in both proliferating and non-proliferating cells (for a review see [37]), allowing to target a wide area for angiostatin production. Thus, a defective adenovirus that expresses the N-terminal fragment (aa 1-333) from human Plg, including its pre-activation peptide and kringles 1 to 3 (AdK3) was constructed.

The use of Mab A1D12, which is specific to human Plg [50] first demonstrated an efficient secretion of angiostatin in the culture media of cells infected with AdK3. The inclusion of the N-terminal pre-activation peptide in the angiostatin molecule did not affect its anti-angiogenic activity since AdK3- but not AdCO1-infected endothelial cells showed a marked, dose-dependent, arrest in proliferation in vitro (FIG. 8A). Furthermore, the proliferation of MDA-MB-231 or C6 tumor cells was not affected by AdK3-infection demonstrating the restricted action of angiostatin for endothelial cells. Virus-free supernatants from AdK3-infected tumor cell culture also inhibited endothelial cell proliferation, illustrating the paracrine effect of angiostatin secreted by transduced-tumor cells.

Because the kringle domains are important for Plg binding to fibrin and fibrin degradation, it was essential to analyze the effect of this therapy in thrombolysis, a physiological protection against thrombosis in vivo. The angiostatin secreted in the culture medium failed to inhibit tPA-induced whole blood clot lysis in vitro. Although this experiment has not excluded the deleterious competition between angiostatin and Plg to bind to fibrin during thrombolysis in vivo, it indicates that an angiostatic effect could be achieved at a concentration far below that required for abrogating plasminogen-dependent thrombolysis in vivo. This may also suggest that endothelial cells exhibit a receptor that recognizes angiostatin and not intact Plg.

Flow cytometry analysis of endothelial cells infected with AdK3 demonstrated a complete disappearance of the mitotic population positive for MPM-2 MAb [56]. Immunoblot analysis revealed that M-phase phosphoproteins reactive to MPM-2 MAb were indeed downregulated in angiostatin-treated endothelial cells, in sharp contrast with control endothelial cells. This observation should be helpful to define the mechanism by which angiostatin abrogates the proliferation of endothelial cells. We also showed that angiostatin disrupted the G2/M transition induced by M-phase-promoting factor (MPF), composed of cdc2 and its associated regulatory subunit, cyclin B [57]. MPF phosphorylated proteins, reactive with MPM-2 MAb, are involved in major alterations of cellular structures and activities for an efficient progression to mitosis. The reason why active MPF was lacking in AdK3-transduced endothelial cells must be further investigated.

A single intratumoral injection of AdK3, but not of AdCO1 was shown to dramatically inhibit primary tumor growth in two pre-established xenograft murine models. This inhibitory effect on tumor growth was tightly correlated with a markedly decreased vascularization within, and at the vicinity of the tumors (FIG. 10), together with the detection of angiostatin-immunoreactive material in the tumor extracts (FIG. 7C). C6 glioma is a highly vascularized tumor due to its VEGF overexpression [58]. Interestingly, the AdK3-transduced C6 glioma apparently failed to establish a vascular network within the tumor mass to support rapid and extensive growth (FIG. 10), and this failure translated to more than 80% inhibition of tumor growth. vWF immunostaining of tumor sections also revealed a significant reduction of neoangiogenesis in the AdK3-treated tumors: well formed vessels with a mature lumen were frequently observed in control C6 tumors, but not in AdK3-treated C6 glioma (FIG. 10). This decrease in vessel density was associated with a 10-fold increase in tumor cells apoptosis and no apparent modification of the tumor cell proliferation index, probably because (i) of the lack of endothelial-derived paracrine factors, (ii) a reduction in nutrient support, and (iii) hypoxia triggered p53-dependent apoptosis of the tumor cells [59, 60]. In the MDA-MB-231 breast carcinoma model, a single intratumoral injection of AdK3 similarly induced a remarkable inhibition of tumor angiogenesis and growth.

In the course of this study, AdK3-transduced C6 and MDA-MB-231 cells exhibited a lower tumorigenic potential as reflected by a prolonged delay for AdK3-infected cells to develop into visible tumors following implantation.

Angiostatic therapy using recombinant adenoviruses has been shown to be experimentally plausible and efficient. The possibility of delivering more than one angiostatic factor could also synergize to arrest tumor growth. It is also envisioned that its association with cytotoxic approaches may be particularly potent to improve the clinical outcome of malignant diseases.

REFERENCES

The following reference citations, which are cited by number in the Background and Examples of the invention, are specifically incorporated herein by reference in their entireties:

1) E. Bacharach, A. Itin and E. Keshet. In vivo patterns of expression of urokinase and its inhibitor PAI-1 suggest a concerted role in regulating physiological angiogenesis. Proc. Natl. Acad. Sci. USA 89, 10686–10690 (1992).
2) P. R. M. Mignatti and D. B. Rifkin. Biology and biochemistry of proteinases in tumor invasion. Physiol. Rev. 73, 161–195. (1993).
3) S. Imren, D. B. Kohn, H. Shimada, L. Blavier and X. DeClerck. Overexpression of tissue inhibitor of metalloproteinases-2 by retroviral-mediated gene transfer in vivo inhibits tumor growth and invasion. Cancer Res. 56, 2891–2895 (1996).
4) M. Ploug, E. Ronne, N. Behrendt, A. L. Jensen and F. Blasi. Cellular receptor for urokinase plasminogen activator: carboxyl-terminal processing and membrane anchoring by glycosylphosphatidylinositol. J. Biol. Chem. 266, 1926–1933 (1991).
5) A. L. Roldan, M. V. Cubellis, M. T. Masucci, N. Behrendt, L. R. Lund, K. Dano, E. Appella and F. Blasi. Cloning and expression of the receptor for human urokinase plasminogen activator, a central molecule in cell surface, plasmin dependent proteolysis. EMBO J. 9, 467–474 (1990).
6) V. Ellis, N. Behrendt and K. Dano. Plasminogen activation by receptor-bound urokinase, a kinetic study with cell-associated and isolated receptor. J. Biol. Chem. 266, 12752–12758 (1991).
7) C. He, S. M. Wilhelm, A. P. Pentland, B. L. Marmer, G. A. Grant, A. Z. Eisen and G. I. Goldberg. Tissue cooperation in a proteolytic cascade activating human interstitial collagenase. Proc. Natl. Acad. Sci. USA 86, 2632–2636 (1989).
8) A. Estreicher, J. Muhlhauser, J. L. Carpentier, L. Orci and J. D. Vassalli. The receptor for urokinase type plasminogen activator polarizes expression of the protease to the leading edge of migrating monocytes and promotes degradation of enzyme inhibitor complexes. J. Cell Biol. 111, 783–792 (1990).
9) Y. Wei, D. A. Waltz, N. Rao, R. J. Drummond, S. Rosenberg and H. A. Chapman. Identification of the urokinase receptor as an adhesion receptor for vitronectin. J. Biol. Chem. 269, 32380–32388 (1994).
10) Y. Wei, M. Lukashev, D. I. Simon, S. C. Bodary, S. Rosenberg, M. V. Doyle and H. A. Chapman. Regulation of integrin function by the urokinase receptor. Science 273, 1551–1555 (1996).
11) L. Naldini, L. Tamagnone, E. Vigna, M. Sachs, G. Hartmann, W. Birchmeier, Y. Daikuhara, H. F. B. Tsubouchi and P. M. Comoglio. Extracellular proteolytic cleavage by urokinase is required for activation of hepatocyte growth factor/scatter factor. EMBO J. 11, 4825–4833 (1992).
12) D. Rifkin, D. Moscatelli, J. Bizik, N. Quarto, F. Blei, P. Dennis, R. Flaumenhaft and P. Mignatti. Growth factor control of extracellular proteolysis. Cell Differ. Dev. 32, 313–318 (1990).

13) M. Schmitt, F. Janicke and H. Graeff. Tumor-associated proteases. Fibrinolysis 6, 3–26 (1992).

14) C. Pyke, P. Kristensen, E. Ralfkiaer, J. Grondhal-Hansen, J. Eriksen, F. Blasi and K. Dano. Urokinase-type plasminogen activator is expressed in stromal cells and its receptor in cancer cells at invasive foci in human colon adenocarcinomas. Am. J. Pathol. 138, 1059–1067 (1991).

15) R. L. Shapiro, J. G. Duquette, D. F. Roses, I. Nunes, M. N. Harris, H. Kamino, E. L. Wilson and D. B. Rifkin. Induction of primary cutaneous melanocytic neoplasms in urokinase-type plasminogen activator (uPA) deficient and wild-type mice: cellular blue Nevi invade but do not progress to malignant melanoma in uPA-deficient animals. Cancer Res. 56, 3597–3604 (1996).

16) D. Belin, J. D. Vassalli, C. Combepine, F. Godeau, Y. Nagamine, E. Reich, H. P. Kocher and R. M. Duvoisin. Cloning, nucleotide sequencing and expression of cDNAs encoding mouse urokinase-type plasminogen activator. Eur. J. Biochem. 148, 225–232 (1985).

17) E. Appella, E. A. Robinson, S. J. Ullrich, M. P. Stoppelli, A. Corti, G. Cassani and F. Blasi. The receptor binding sequence of urokinase: a biological function for the growth factor module of proteases. J. Biol. Chem. 262, 4437–4440 (1987).

18) V. Magdolen, P. Rettenberger, M. Koppitz, L. Goretski, H. Kessler, U. H. Weidle, B. Konig, H. Graeff, M. Schmitt and O. Wilhelm. Systemic mutational analysis of the receptor-binding region of the human urokinase-type plasminogen activator. Eur. J. Biochem. 237, 743–751 (1996).

19) H. Lu, P. Yeh, J. D. Guitton, C. Mabilat, F. Desanlis, 1. Maury, Y. Legrand, J. Soria and C. Soria. Blockage of the urokinase receptor on the cell surface: construction and characterization of a hybrid protein consisting of the N-terminal fragment of human urokinase and human albumin. FEBS Lett. 356, 56–59 (1994).

20) C. W. Crowley, R. L. Cohen, B. K. Lucas, G. Liu, M. A. Shuman and A. D. Levinson. Prevention of metastasis by inhibition of the urokinase receptor. Proc. Natl. Acad. Sci. U.S.A. 90, 5021–5025 (1993).

21) H. Kobayashi, J. Gotoh, M. Fujie, H. Shinohara, N. Moniwa and T. Terao. Inhibition of metastasis of Lewis lung carcinoma by a synthetic peptide within the growth factor-like domain of urokinase in an experimental and spontaneous metastasis modellnt. J. Cancer 57, 727–733 (1994).

22) H. Lu, C. Mabilat, P. Yeh, J. D. Guitton, H. Li, M. Pouchelet, D. Shoevaert, Y. Legrand, J. Soria and C. Soria. Blockage of urokinase receptor reduces in vitro the motility and deformability of endothelial cells. FEBS Lett. 380, 21–24 (1996).

23) H. Y. Min, L. V. Doyle, C. R. Vitt, C. L. Zandonella, J. R. Stratton-Tomas, M. A. Shuman and S. Rosenberg. Urokinase receptor antagonists inhibit angiogenesis and primary tumor growth in syngenic mice. Cancer Res. 56, 2428–2433 (1996).

24) J. Folkman. Angiogenesis in cancer, vascular, rheumatoid and other disease. Nature Medicine 1, 27–31. (1995).

25) L. D. Stratford-Perricaudet, I. Makeh, M. Perricaudet and P. Briand. Widespread long-term gene transfer to mouse skeletal muscles and heart via an adenovirus vector. J. Clin. Invest. 90, 626–630 (1992).

26) B. Hirt. Selective extraction of polyoma DNA from infected mouse cells cultures. J. Mol. Biol. 26, 365–369 (1967).

27) F. L. Graham, J. Smiley, W. C. Russel and R. Nairn. Characteristics of a human cell line transformed by DNA from human adenovirus type 5J. Gen. Virol. 36, 59–72 (1977).

28) N. Weidner, J. P. Semple and W. R. Welch. Tumor angiogenesis and metastasis-correlation in invasive breast carcinoma. N. Engl. J. Med. 324, 1–8 (1991).

29) J.-F. Dedieu, E. Vigne, C. Torrent, C. Jullien, 1. Mahfouz, J.-M. Caillaud, N. Aubailly, C. Orsini, J. M. Guillaume, P. Opolon, P. Delaère, M. Perricaudet and P. Yeh. Long-term gene delivery into the liver of immuno-competent mice with E1/E4-defective adenoviruses. J. Virol. (1997).

30) T. J. Wickham, P. Mathias, D. A. Cheresh and G. R. Nemerow. Integrins avb3 and avb5 promote internalization but not virus attachment. Cell 73, 309–319 (1993).

31) P. C. Brooks, A. M. P. Montgomery, M. Rosenfeld, R. A. Reisfeld, T. Hu, G. Klier and D. A. Cheresh. Integrin aVb3 antagonists promote tumor regression by inducing apoptosis of angiogenic blood vessels. Cell 79, 1157–1164 (1994).

32) M. O'Reilly, L. Holmgren, Y. Shing, C. Chen, R. Rosenthal, M. Moses, W. Lane, Y. Cao, E. Sage and J. Folkman. Angiostatin: a novel angiogenesis inhibitor that mediates the suppression of metastases by a Lewis lung carcinoma. Cell 79, 315–328 (1994).

33) T. P. D. Fan, R. Jaggar and R. Bicknell. Controlling the vasculature: angiogenesis, anti-angiogenesis and vascular targeting of gene therapy. TIPS 16, 57–66 (1995).

34) L. Holmgren, M. S. O'Reilly and J. Folkman. Dormancy of micrometastasis: balanced proliferation and apoptosis in the presence of angiogenesis suppression. Nature Med. 1, 149–153 (1995).

35) H. F. Dvorak, J. A. Nagy, J. T. Dvorak and A. M. Dvorak. Identification and characterization of the blood vessels of solid tumors that are leaky to circulating macromolecules. Am. J. Pathol. 133, 95–109 (1988).

36) L. Liotta, J. Kleinerman and G. Saidel. Quantitative relationships of intravascular tumor cells, tumor vessels and pulmonary metastases following tumor implantation. Cancer Res. 34, 997–1004 (1974).

37) P. Yeh and M. Perricaudet. Advances in adenoviral vectors: from genetic engineering to their biology. FASEB J. 11:615–623 (1997).

38) J. Folkman. What is the evidence that tumors are angiogenesis dependent. *J. Natl. Cancer Inst*. 82, 4–6 (1990).

39) D. Hanahan & J. Folkman. Patterns and emerging mechanisms of the angiogenic switch during tumorigenesis. *Cell* 86, 353–364 (1996).

40) A. Hori. Suppression of solid tumor growth by immunoneutralizing monoclonal antibody against human basic fibroblast growth factor. *Cancer Res*. 51, 6180–6184 (1991).

41) K. J. Kim. Inhibition of vascular endothelial growth factor-induced angiogenesis suppresses tumour growth in vivo. *Nature* 362, 841–844 (1993).

42) M. O. O'Reilly, T. Boehm, Y. Shing, N. Fukai, G. Vasios, W. S. Lane, E. Flynn, J. R. Birkhead, B. R., Olsen, & J. Folkman. Endostatin: An Endogenous Inhibitor of Angiogenesis and tumor Growth. *Cell* 88, 277–285 (1997).

43) C. Clapp, J. A. Martial, R. C. Guzman, F. Rentier-Deirue, & R. I. Weiner. The 16 kDa N-terminal fragment of human prolactin is a potent inhibitor of angiogenesis. *Endocrinol*. 133, 1292–1299 (1993).

44) S. K. Gupta, T. Hassel, & J. P. Singh. A potent inhibitor of endothelial cell proliferation is generated by proteolytic cleavage of the chemokine platelet factor 4. *Proc. Natl. Acad. Sci. USA*. 92, 7799–7803 (1995).
45) Z. Dong, R. Kumar, X. Yang, & I. Fidler. Macrophage-derived metalloelastase is responsible for the generation of angiostatin in Lewis Lung Carcinoma. *Cell* 88, 801–810 (1997).
46) M. O'Reilly, L. Holmgren, C. Chen, & J. Folkman. Angiostatin induces and sustains dormancy of human primary tumors in mice. *Nature Med*. 2, 689–692 (1996).
47) Y. Cao, R. W. Ji, D. Davidson, J. Schaller, D. Marti, S. Söhndel, S. G. McCance, M. S. O'Reilly, M. Llinas, & J. Folkman. Kringle domains of human angiostatin. *J. Biol. Chem.* 271, 29461–29467 (1996).
48) J. A. Roth & R. J. Christiano. Gene therapy for cancer: what have we done and where are we going. *J. Natl. Cancer Inst.* 88, 21–39 (1997).
49) V. Trochon, C. Mabilat, P. Bertrand, Y. Legrand, F. Smadja-Joffe, C. Soria, B. Delpech & H. Lu. Evidence of involvement of CD44 in endothelial cell proliferation, migration and angiogenesis in vitro. *Int. J. Cancer* 66, 664–668 (1996).
50) M. Mirshahi, J. Soria, H. R. Lijnen, V. Fleury, O. Bertrand, J. Y. Drouet, J. Caen & C. Soria. A monoclonal antibody directed against an epitope in the NH2-terminal region of native human plasminogen induces a modification of its functional properties. *fibrinolysis and Coagulation, in press* (1997).
51) M. S. Pepper, R. Montesano, J. D. Vassalli & L. Orli. Chondrocytes inhibits endothelial sprout formation in vitro: evidence for involvement of a transforming growth factor β. *J. cell. Physiol.* 146, 170–179(1991).
52) M. Mirshahi, J. C. S. Soria, R. Faivre, H. Lu, M. Courtney, C. Roitsch, D. Tripier & J. P. Caen. Evaluation of the inhibition by heparin and hirudin of coagulation activation by r-tPA induced thrombolysis. *Blood* 74, 1025–1030 (1989).
53) A. Skladanowski & A. K. Larsen. Expression of Wild-type p53 etoposide cytotoxicity in M1 myeloid leukemia cells by facilitated G2 to M transition: Implications for gene therapy. *Cancer Res.* 57, 818–823 (1997).
54) B. K. Lee Sim, M. S. O'Reilly, H. Liang, A. H. Fortier, W. He, J. W. Madsen, R. Lapcevich & C. A. Nacy. A recombinant human angiostatin protein inhibits experimental primary and metastatic cancer. *Cancer Res.* 57, 1329–1334 (1997).
55) M. L. Hayes & F. J. Castellino. Carbohydrate of the human plasminogen variant II. Structure of the asparagine-linked oligosaccharide unit. *J. Biol. Chem.* 254, 8772–8776 (1979).
56) F. M. Davis, T. Y. Tsao, S. K. Fowler & P. N. Rao. Monoclonal antibodies to mitotic cells. *Proc. Natl. Acad. Sci.* 80, 2926–2930 (1983).
57) R. W. King, P. K. Jackson & M. W. Kirschner. Mitosis in transition. *Cell* 18, 563–571 (1994).
58) K. H. Plate, G. Breier, H. A. Weich & W. Risau. Vascular endothelial growth factor is a potential tumor angiogenesis factor in human gliomas in vivo. *Nature* 359, 845–848 (1992).
59) J. Hamada, P. G. Cavanaugh, O. Lotan & G. L. Nicolson. Separate growth and migration factors for large-cell lymphoma cells secreted by microvascular endothelial cells derived from target organs for metastasis. *Br. J. Cancer* 66, 349–354 (1992).
60) G. G. Graeber. Hypoxia-mediated selection of cells with diminished apoptotic potential in solid tumors. *Nature* 379, 88–91 (1996).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method for inhibiting the growth or metastasis or both of a tumor comprising introducing a vector into the tumor, the vector comprising a nucleic acid sequence encoding an amino terminal fragment of urokinase that comprises an EGF-like domain, with the exception that the nucleic acid sequence does not encode full length urokinase, wherein the nucleic acid sequence is operably associated with an expression control sequence that provides for expression in a cell of the tumor.

2. The method of claim 1 wherein the expression control sequence comprises a CMV promoter.

3. A method for inhibiting the growth of a tumor comprising introducing into the tumor a defective adenovirus vector comprising a DNA sequence encoding an anti-angiogenic factor operably associated with an expression control sequence that provides for expression of the anti-angiogenic factor in a cell of the tumor, wherein the anti-angiogenic factor comprises an amino terminal fragment of urokinase that comprises an EGF-like domain, with the exception that the anti-angiogenic factor is not full length urokinase.

4. The method of claim 3, wherein the expression control sequence comprises a CMV promoter.

5. The method of claim 3, wherein the adenovirus vector contains a deletion in the E1 region.

6. The method of claim 5, wherein the expression control sequence comprises a CMV promoter.

7. A defective adenovirus vector comprising a gene encoding an anti-angiogenic factor operably associated with an expression control sequence, wherein the anti-angiogenic factor comprises an amino terminal fragment of urokinase comprising an EGF-like domain, with the exception that the anti-angiogenic factor is not full length urokinase.

8. The vector of claim 7, wherein the expression control sequence comprises a CMV promoter.

9. The vector of claim 7, wherein the adenovirus vector contains a deletion in the E1 region.

10. The vector of claim 9, wherein the expression control sequence comprises a CMV promoter.

11. A pharmaceutical composition comprising the defective adenovirus vector according to claim 7 and a pharmaceutically acceptable carrier.

12. A pharmaceutical composition comprising the defective adenovirus vector according to claim 8 and a pharmaceutically acceptable carrier.

13. A pharmaceutical composition comprising the defective adenovirus vector according to claim 9 and a pharmaceutically acceptable carrier.

14. A pharmaceutical composition comprising the defective adenovirus vector according to claim 10 and a pharmaceutically acceptable carrier.

* * * * *